(12) United States Patent
Rossi et al.

(10) Patent No.: US 8,030,290 B2
(45) Date of Patent: Oct. 4, 2011

(54) CELL-TYPE SPECIFIC APTAMER-SIRNA DELIVERY SYSTEM FOR HIV-1 THERAPY

(75) Inventors: John J. Rossi, Alta Loma, CA (US); Jiehua Zhou, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 12/328,994

(22) Filed: Dec. 5, 2008

(65) Prior Publication Data

US 2009/0148944 A1   Jun. 11, 2009

Related U.S. Application Data

(60) Provisional application No. 60/996,850, filed on Dec. 7, 2007.

(51) Int. Cl.
*A01N 43/04* (2006.01)
*A61K 31/70* (2006.01)
*C07H 21/04* (2006.01)

(52) U.S. Cl. ........................................ 514/44; 536/24.5
(58) Field of Classification Search ............... 514/44; 536/24.5
See application file for complete search history.

(56) References Cited

U.S. PATENT DOCUMENTS

| 6,706,266 | B1 * | 3/2004 | Life ........................... 424/139.1 |
| 2004/0096843 | A1 | 5/2004 | Rossi et al. |
| 2005/0222400 | A1 * | 10/2005 | Prasad et al. .................. 536/23.1 |
| 2005/0256071 | A1 * | 11/2005 | Davis ............................. 514/44 |
| 2006/0105975 | A1 * | 5/2006 | Pendergrast et al. ........... 514/44 |
| 2008/0064647 | A1 * | 3/2008 | Guo et al. ....................... 514/44 |

FOREIGN PATENT DOCUMENTS

WO   2007/143086 A2   12/2007

OTHER PUBLICATIONS

McNamara et al., "Cell type-specific delivery of siRNAs with aptamer siRNA chimeras," Nature Biotechnology 24(8): 1005-1015 (2006).
Third Party Submission dated Aug. 10, 2009, John J. Rossi et al., U.S. Appl. No. 12/328,994, 5 pages.
Makobetsa Khati et al., "Neutralization of Infectivity of Diverse R5 Clinical Isolates of Human Immunodeficiency Virus Type 1 by gp120-Binding 2'F-RNA Aptamers," Journal of Virology, Dec. 2003, vol. 77, No. 23, pp. 12692-12698, Copyright 2003, American Society for Microbiology, 7 pages.

* cited by examiner

*Primary Examiner* — Brian Whiteman
(74) *Attorney, Agent, or Firm* — Rothwell, Figg, Ernst & Manbeck PC

(57) ABSTRACT

The present invention relates to compositions and methods for delivery of siRNA to specific cells or tissue. More particularly, the present invention relates to compositions and methods for cell type-specific delivery of anti-HIV siRNAs via fusion to an anti-gp120 aptamer.

5 Claims, 20 Drawing Sheets

5'- GGA CAC TGA CAT GGA CTG AAG
GAG TAG AAA GAG CTC ATC AGA ACA GTC AGA CTG ATC AAG CTT CTC TAT CAA
AGC AAC CCA CCT CCC AAT CCC GAG GGG ACG CGT CAG GCG CGC AGG AAT
AGA AGG CGC CGG TGG AGA GAG AGA CAG AGA CAG ATC CAT TCG ATA TCT
GAA CGG ATC CTT GGC ACT TAT CTG GGA CGA TCT GCA GAG CCT GTG CCT CTT
CAG CTA CCA CCG CTT GAG AGG TTA-3'

FIG. 9A

5'- GGA CAC TGA CAT GGA CTG AAG GAG TAG AAA GAC GAA GAG CTC ATC AGA
ACA GTC AGA CTG ATC AAG CTT CTC TAT CAA AGC AAC CCA CCT CCC AAT CCC
GAG GGG ACG CGT CAG GCG CGC AGG AAT AGA AGG CGC CGG TGG AGA GAG
AGA CAG AGA CAG ATC CAT TCG ATA TCT GAA CGG ATC CTT GGC ACT TAT CTG
GGA CGA TCT GCA GAG CCT GTG CCT CTT CAG CTA CCA CCG CTT GAG AGG TTA-
3'

FIG. 9B

TARGET SITE 1
TTGACCTCCATAGAAGACACCGGGACCGATCCAGCCTCCGCCGGCGCGCAAGAAATGGCTAGCGCAGGAAGAAGCGGAGACAGC
GACGAAGAGCTCATCAGAACAGTCAGACTGATCAAGCTTCTCTATCAAAGCAACCCACCTCCAATCCCGAGGGGACGCGTCAG
GCGCGCAGGAATAGAAGGCGCCGGTGGAGAGAGAGACAGAGACAGATCCATTCGATATCTGAACGGATCCTTGGCACTTATCTGGGA
CGATCTGCAGAGCCTGTGCCTCTTCAGCTACCACCGCTTGAGAGGTTAACTCTTGATTGTAACGAGGATTGTGGAACTAGTGGGACACA
GGGTGTGGGGTCACCTCAAATATTGGTGGAATCTCCTACAGTACTCGAGTCAGGAACTAAAGAGAATGGTGCAGGAGCTAGCAAAGGA
GAAGAACTCTTCACTGGAGTTGTCCCAATTCTTGTTGAATTAGATGGTGATGTTAACGGCCACAAGTTCTCTGTCAGTGGAGAGGGTGA
GSP PRIMER 2
GSP PRIMER 1
27 mer DUPLEX RNA:
RACE PCR 5'- ADAPTOR PRODUCT: 243 bp
21 mer DUPLEX RNA:
RACE PCR 5'-ADAPTOR PRODUCT: 249 bp

FIG. 9C

SEQUENCE LISTING

<160> NUMBER OF SEQ ID NOS: 33

<210> SEQ ID NO 1
<211> LENGTH: 108
<212> TYPE: RNA
<213> ORGANISM: Artificial
<220> FEATURE:
<223> OTHER INFORMATION: Anti-gp120 aptamer-siRNA sense strand chimera

<400> SEQUENCE: 1
gggagacaag acuagacgcu caaugugggc cacgcccgau uuuacgcuuu uacccgcacg    60

```
cgauugguuu guuuccccuc ugcggagaca gcgacgaaga gcucauca                        108
```

<210> SEQ ID NO 2
<211> LENGTH: 29
<212> TYPE: DNA
<213> ORGANISM: Artificial
<220> FEATURE:
<223> OTHER INFORMATION: anti-tat/rev 27 mer siRNA antisense strand
<220> FEATURE:
<221> NAME/KEY: misc_feature
<222> LOCATION: (1)..(29)
<223> OTHER INFORMATION: nucleotides 1-27 are RNA and nucleotides 28-29
      are DNA

<400> SEQUENCE: 2

```
ugaugagcuc uucgucgcug ucuccgctt                                             29
```

<210> SEQ ID NO 3
<211> LENGTH: 23
<212> TYPE: DNA
<213> ORGANISM: Artificial
<220> FEATURE:
<223> OTHER INFORMATION: anti-tat/rev 21 mer siRNA antisense strand
<220> FEATURE:
<221> NAME/KEY: misc_feature
<222> LOCATION: (1)..(23)
<223> OTHER INFORMATION: nucleotides 1-21 are RNA and nucleotides 22-23
      are DNA

<400> SEQUENCE: 3

```
gcucuucguc gcugucuccg ctt                                                   23
```

<210> SEQ ID NO 4
<211> LENGTH: 27
<212> TYPE: DNA
<213> ORGANISM: Artificial
<220> FEATURE:
<223> OTHER INFORMATION: HIV-1 Tat/Rev target sequence

<400> SEQUENCE: 4

```
gcggagacag cgacgaagag ctcatca                                               27
```

<210> SEQ ID NO 5
<211> LENGTH: 243
<212> TYPE: DNA
<213> ORGANISM: Artificial
<220> FEATURE:
<223> OTHER INFORMATION: 27 mer duplex RNA, RACE PCR product

<400> SEQUENCE: 5

```
ggacactgac atggactgaa ggagtagaaa gagctcatca gaacagtcag actgatcaag           60
cttctctatc aaagcaaccc acctcccaat cccgagggga cgcgtcaggc gcgcaggaat          120
agaaggcgcc ggtggagaga gagacagaga cagatccatt cgatatctga acgatccttt          180
ggcacttatc tgggacgatc tgcagagcct gtgcctcttc agctaccacc gcttgagagg          240
tta                                                                        243
```

<210> SEQ ID NO 6
<211> LENGTH: 249
<212> TYPE: DNA
<213> ORGANISM: Artificial
<220> FEATURE:
<223> OTHER INFORMATION: 21 mer duplex RNA, RACE PCR product

<400> SEQUENCE: 6

```
ggacactgac atggactgaa ggagtagaaa gacgaagagc tcatcagaac agtcagactg           60
```

```
atcaagcttc tctatcaaag caacccacct cccaatcccg aggggacgcg tcaggcgcgc      120
aggaatagaa ggcgccggtg gagagagaga cagagacaga tccattcgat atctgaacgg      180
atccttggca cttatctggg acgatctgca gagcctgtgc ctcttcagct accaccgctt      240
gagaggtta                                                              249

<210> SEQ ID NO 7
<211> LENGTH: 521
<212> TYPE: DNA
<213> ORGANISM: Human immunodeficiency virus

<400> SEQUENCE: 7
ttgacctcca tagaagacac cgggaccgat ccagcctccg cgggcgcgca agaaatggct       60
agcgcaggaa gaagcggaga cagcgacgaa gagctcatca gaacagtcag actgatcaag      120
cttctctatc aaagcaaccc acctcccaat cccgagggga cgcgtcaggc gcgcaggaat      180
agaaggcgcc ggtggagaga gagacagaga cagatccatt cgatatctga acggatcctt      240
ggcagttatc tgggacgatc tgcagagcct gtgcctcttc agctaccacc gcttgagagg      300
ttaactcttg attgtaacga ggattgtgga actagtggga cacagggtgt ggggtcacct      360
caaatattgg tggaatctcc tacagtactc gagtcaggaa ctaaagagaa tggtgcagga      420
gctagcttag gagaagaact cttcactgga gttgtcccaa ttcttgttga attagatggt      480
gatgttaacg ccacaagtt ctctgtcagt ggagagggtg a                           521

<210> SEQ ID NO 8
<211> LENGTH: 81
<212> TYPE: RNA
<213> ORGANISM: Artificial
<220> FEATURE:
<223> OTHER INFORMATION: Anti-gp120 aptamer A1

<400> SEQUENCE: 8
gggaggacga ugcggaauug agggaccacg cgcugcuugu ugugauaagc aguuugucgu       60
gauggcagac gacucgcccg a                                                81

<210> SEQ ID NO 9
<211> LENGTH: 81
<212> TYPE: RNA
<213> ORGANISM: Artificial
<220> FEATURE:
<223> OTHER INFORMATION: Anti-gp120 aptamer B-68

<400> SEQUENCE: 9
gggaggacga ugcggacaua guaaugacac ggaggaugga gaaaaaacag ccaucucuug       60
acggucagac gacucgcccg a                                                81

<210> SEQ ID NO 10
<211> LENGTH: 27
<212> TYPE: RNA
<213> ORGANISM: Artificial
<220> FEATURE:
<223> OTHER INFORMATION: Anti-tat/rev 27 mer siRNA sense strand

<400> SEQUENCE: 10
gcggagacag cgacgaagag cucauca                                          27

<210> SEQ ID NO 11
<211> LENGTH: 21
<212> TYPE: RNA
<213> ORGANISM: Artificial
```

```
<220> FEATURE:
<223> OTHER INFORMATION: Anti-tat/rev 21 mer siRNA sense strand

<400> SEQUENCE: 11
gcggagacag cgacgaagag c                                              21

<210> SEQ ID NO 12
<211> LENGTH: 77
<212> TYPE: RNA
<213> ORGANISM: Artificial
<220> FEATURE:
<223> OTHER INFORMATION: Anti-gp120 aptamer

<400> SEQUENCE: 12
gggagacaag acuagacgcu caauguggcc cacgcccgau uuuacgcuuu uacccgcacg    60
cgauugguuu guuuccc                                                   77

<210> SEQ ID NO 13
<211> LENGTH: 104
<212> TYPE: RNA
<213> ORGANISM: Artificial
<220> FEATURE:
<223> OTHER INFORMATION: Anti-gp120 aptamer-siRNA sense strand chimera

<400> SEQUENCE: 13
gggagacaag acuagacgcu caauguggcc cacgcccgau uuuacgcuuu uacccgcacg    60
cgauugguuu guuucccgcg gagacagcga cgaagagcuc auca                    104

<210> SEQ ID NO 14
<211> LENGTH: 102
<212> TYPE: RNA
<213> ORGANISM: Artificial
<220> FEATURE:
<223> OTHER INFORMATION: Anti-gp120 aptamer-siRNA sense strand chimera

<400> SEQUENCE: 14
gggagacaag acuagacgcu caauguggcc cacgcccgau uuuacgcuuu uacccgcacg    60
cgauugguuu guuucccuc ugcggagaca gcgacgaaga gc                       102

<210> SEQ ID NO 15
<211> LENGTH: 98
<212> TYPE: RNA
<213> ORGANISM: Artificial
<220> FEATURE:
<223> OTHER INFORMATION: Anti-gp120 aptamer-siRNA sense strand chimera

<400> SEQUENCE: 15
gggagacaag acuagacgcu caauguggcc cacgcccgau uuuacgcuuu uacccgcacg    60
cgauugguuu guuucccgcg gagacagcga cgaagagc                            98

<210> SEQ ID NO 16
<211> LENGTH: 108
<212> TYPE: RNA
<213> ORGANISM: Artificial
<220> FEATURE:
<223> OTHER INFORMATION: Anti-gp120 aptamer-siRNA sense strand chimera

<400> SEQUENCE: 16
gggagacaag acuagacgcu caauguggc ggggcccgau uuuaccguuu ucaaagcacg     60
cgauugguuu guuucccuc ugcggagaca gcgacgaaga gcucauca                 108

<210> SEQ ID NO 17
<211> LENGTH: 108
```

```
<212> TYPE: RNA
<213> ORGANISM: Artificial
<220> FEATURE:
<223> OTHER INFORMATION: Anti-gp120 aptamer-siRNA sense strand chimera

<400> SEQUENCE: 17
gggagacaag acuagacgcu caaugugggc cacgcccgau uuuacgcuuu uacccgcacg     60
cgauugguuu guuucccuc ugcggagaca gcguguaaga gcucauca                 108

<210> SEQ ID NO 18
<211> LENGTH: 29
<212> TYPE: DNA
<213> ORGANISM: Artificial
<220> FEATURE:
<223> OTHER INFORMATION: anti-tat/rev 27 mer siRNA antisense strand
<220> FEATURE:
<221> NAME/KEY: misc_feature
<222> LOCATION: (1)..(29)
<223> OTHER INFORMATION: nucleotides 1-27 are RNA and nucleotides 28-29
      are DNA

<400> SEQUENCE: 18
ugaugagcuc uuacacgcug ucuccgctt                                      29

<210> SEQ ID NO 19
<211> LENGTH: 26
<212> TYPE: DNA
<213> ORGANISM: Artificial
<220> FEATURE:
<223> OTHER INFORMATION: reverse transcription GSP primer

<400> SEQUENCE: 19
tcaccctctc cactgacaga gaactt                                         26

<210> SEQ ID NO 20
<211> LENGTH: 26
<212> TYPE: DNA
<213> ORGANISM: Artificial
<220> FEATURE:
<223> OTHER INFORMATION: PCR GSP forward primer

<400> SEQUENCE: 20
ggacactgac atggactgaa ggagta                                         26

<210> SEQ ID NO 21
<211> LENGTH: 26
<212> TYPE: DNA
<213> ORGANISM: Artificial
<220> FEATURE:
<223> OTHER INFORMATION: PCR GSP reverse primer

<400> SEQUENCE: 21
taacctctca agcggtggta gctgaa                                         26

<210> SEQ ID NO 22
<211> LENGTH: 20
<212> TYPE: DNA
<213> ORGANISM: Artificial
<220> FEATURE:
<223> OTHER INFORMATION: RT-PCR tat/rev forward primer

<400> SEQUENCE: 22
ggcgttactc gacagaggag                                                20

<210> SEQ ID NO 23
<211> LENGTH: 23
<212> TYPE: DNA
```

```
<213> ORGANISM: Artificial
<220> FEATURE:
<223> OTHER INFORMATION: RT-PCR tat/rev reverse primer

<400> SEQUENCE: 23
tgctttgata gagaagcttg atg                                          23

<210> SEQ ID NO 24
<211> LENGTH: 19
<212> TYPE: DNA
<213> ORGANISM: Artificial
<220> FEATURE:
<223> OTHER INFORMATION: RT-PCR GADPH forward primer

<400> SEQUENCE: 24
cattgacctc aactacatg                                               19

<210> SEQ ID NO 25
<211> LENGTH: 19
<212> TYPE: DNA
<213> ORGANISM: Artificial
<220> FEATURE:
<223> OTHER INFORMATION: RT-PCR GADPH reverse primer

<400> SEQUENCE: 25
tctccatggt ggtgaagac                                               19

<210> SEQ ID NO 26
<211> LENGTH: 22
<212> TYPE: DNA
<213> ORGANISM: Artificial
<220> FEATURE:
<223> OTHER INFORMATION: RT-PCR IFN-beta forward primer

<400> SEQUENCE: 26
agacttacag gttacctccg aa                                           22

<210> SEQ ID NO 27
<211> LENGTH: 22
<212> TYPE: DNA
<213> ORGANISM: Artificial
<220> FEATURE:
<223> OTHER INFORMATION: RT-PCR IFN-beta reverse primer

<400> SEQUENCE: 27
agacttacag gttacctccg aa                                           22

<210> SEQ ID NO 28
<211> LENGTH: 22
<212> TYPE: DNA
<213> ORGANISM: Artificial
<220> FEATURE:
<223> OTHER INFORMATION: RT-PCR P56 forward primer

<400> SEQUENCE: 28
gcctccttgg gttcgtctat aa                                           22

<210> SEQ ID NO 29
<211> LENGTH: 20
<212> TYPE: DNA
<213> ORGANISM: Artificial
<220> FEATURE:
<223> OTHER INFORMATION: RT-PCR P56 reverse primer

<400> SEQUENCE: 29
ctcagggccc gctcatagta                                              20
```

```
<210> SEQ ID NO 30
<211> LENGTH: 22
<212> TYPE: DNA
<213> ORGANISM: Artificial
<220> FEATURE:
<223> OTHER INFORMATION: RT-PCR OAS 1 forward primer

<400> SEQUENCE: 30
ggaggttgca gtgccaacga ag                                           22

<210> SEQ ID NO 31
<211> LENGTH: 22
<212> TYPE: DNA
<213> ORGANISM: Artificial
<220> FEATURE:
<223> OTHER INFORMATION: RT-PCR Oas 1 reverse primer

<400> SEQUENCE: 31
tggaagggag gcagggcata ac                                           22

<210> SEQ ID NO 32
<211> LENGTH: 110
<212> TYPE: RNA
<213> ORGANISM: Artificial
<220> FEATURE:
<223> OTHER INFORMATION: Anti-gp120 aptamer-siRNA sense strand chimera

<400> SEQUENCE: 32
gggaggacga ugcggaauug agggaccacg cgcugcuugu ugugauaagc aguuugucgu   60
gauggcagac gacucgcccg auugcggaga cagcgacgaa gagcucauca              110

<210> SEQ ID NO 33
<211> LENGTH: 110
<212> TYPE: RNA
<213> ORGANISM: Artificial
<220> FEATURE:
<223> OTHER INFORMATION: Anti-gp120 aptamer-siRNA sense strand chimera

<400> SEQUENCE: 33
gggaggacga ugcggacaua guaaugacac ggaggaugga gaaaaaacag ccaucucuug   60 acgucagac gacucgcccg auugcggaga cagcgacgaa gagcucauca               110
```

CELL-TYPE SPECIFIC APTAMER-SIRNA DELIVERY SYSTEM FOR HIV-1 THERAPY

CROSS-REFERENCE TO RELATED APPLICATION

The present application is related to and claims priority under 35 U.S.C. §119(e) to U.S. provisional patent application Ser. No. 60/996,850 filed 7 Dec. 2007, incorporated herein by reference.

STATEMENT OF FEDERALLY SPONSORED RESEARCH

The present invention was made in part with Government support under Grant Numbers AI29329 awarded by the National Institutes of Health, Bethesda, Md. The Government has certain rights in this invention.

BACKGROUND OF THE INVENTION

The present invention relates to compositions and methods for delivery of siRNA to specific cells or tissue. More particularly, the present invention relates to compositions and methods for cell type-specific delivery of anti-HIV siRNAs via fusion to an anti-gp120 aptamer.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

RNA interference (RNAi) is a process of sequence-specific post-transcriptional gene silencing triggered by small interfering RNAs (siRNA). The silencing is sequence specific and one of the two strands of the siRNA guides the RNA induced silencing complex (RISC) to the complementary target, resulting in cleavage and subsequent destruction of the target RNA (1). RNAi is rapidly becoming one of the methods of choice for gene function studies, and is also being exploited for therapeutic applications (2, 3). The successful therapeutic applications of RNAi are critically dependent upon efficient intracellular delivery of siRNAs (3).

Currently, there are several methods to deliver siRNA in vivo. These can be divided into physical and mechanical methods (hydrodynamic tail vein injections in mice (4-6), electroporation (7-9), ultrasound (10), and the gene gun (11)); local administration (3) (intravenous injection (12), intraperitoneal injection, subcutaneous injection); and chemical methods (cationic lipids (13, 14), polymers (15-20), and peptides (21-24)). However, the delivery efficiency (desired dose), uncontrollable biodistribution and delivery-related toxicities must be carefully analyzed.

Recently, the cell type-specific delivery of siRNAs has been achieved using aptamer-siRNA chimeras (25). In this system, the aptamer portion mediated binding to the prostate-specific membrane antigen (PSMA), a cell-surface receptor and the siRNAs linked to the aptamer was selectively delivered into PSMA expressing cells resulting in silencing of target transcripts both in cell culture and in vivo following intratumoral delivery. In a similar study (26) a modular streptavidin bridge was used to connect lamin A/C or GAPDH siRNAs to the PSMA aptamer. Consequently, this system induced silencing of the targeted genes only in cells expressing the PSMA receptor.

Thus, it is desired to develop compositions and methods for cell- or tissue-specific delivery of siRNA molecules for treatment.

SUMMARY OF THE INVENTION

The present invention relates to compositions and methods for delivery of siRNA to specific cells or tissue. More particularly, the present invention relates to compositions and methods for cell type-specific delivery of anti-HIV siRNAs via fusion to an anti-gp120 aptamer.

In one aspect, the present invention provides a molecule for delivering siRNA to cells or tissues. In one embodiment, the molecule comprises the fusion of an aptamer that is specific for a cell or tissue with a siRNA to be delivered to the cell or tissue. In another embodiment, the aptamer is an anti-gp120 aptamer and the siRNA is directed against HIV-1. In a further embodiment, the siRNA is an anti-tat/rev siRNA. In one embodiment, the aptamer-sense strand siRNA is encoded by a DNA template. In another embodiment, the DNA template is transcribed to produce the aptamer-sense strand siRNA molecule. In a further embodiment, the aptamer-sense strand siRNA is annealed with an antisense strand siRNA to produce the aptamer-siRNA molecule. In one embodiment, pharmaceutical compositions comprising the aptamer-siRNA molecule are provided.

In a second aspect, the present invention provides a method for delivery of siRNA to specific cells or tissue. In one embodiment, the method comprises administering a pharmaceutical composition comprising a molecule for delivering siRNA to cells or tissues. In one embodiment, the molecule comprises the fusion of an aptamer that is specific for a cell or tissue with a siRNA to be delivered to the cell or tissue. In another embodiment, the aptamer is an anti-gp120 aptamer and the siRNA is directed against HIV-1. In a further embodiment, the siRNA is an anti-tat/rev siRNA. In another embodiment, the anti-gp120 aptamer-siRNA is delivered to HIV infected cells.

BRIEF DESCRIPTION OF THE FIGURES

FIG. 3A: Chimera sense strands (SEQ ID NO:1) were annealed with equal molar equivalents of 5'-end $P^{32}$-labeled antisense oligos (SEQ ID NO:2). The FIG. 3B: The cleavage products or denatured strands were visualized following denaturing polyacrylamide-gel electrophoresis. Note that the major Dicer product (marked by a white arrow) of the 27 mer aptamers is processed from the 5' end of the antisense strand since the 21 base product harbors the 5' $^{32}$P label.

FIGS. 9A-9C show the RACE PCR sequences. FIG. 9A: For the 27 mer duplex RNA, the RACE PCR product was cloned into TA vector and sequenced. The resulting sequence is identified as "RACE PCR Product exact sequence (243 bp)" and is SEQ ID NO:5. FIG. 9B: For the 21 mer duplex RNA, the RACE PCR product was gel purified and directly sequenced using relative forward primer (5'-cDNA primer 1) and reverse primer (GSP primer 2). The resulting sequence is identified as "RACE PCR Product exact sequence (249 bp)" and is SEQ ID NO:6. FIG. 9C: The positions of the various sequences within the HIV-1 nucleic acid sequence (SEQ ID NO:7) is shown.

FIG. 11A: The predicated secondary structures of anti-gp120 aptamer A-1 (SEQ ID NO:8) and B-68 (SEQ ID NO:9). FIG. 11B: Gel shift assay. The 5'-end P$^{32}$ labeled individual aptamer was incubated with the increasing gp120 protein. The binding reaction mixtures were preformed gel shift assay. FIG. 11C: The first K$_d$ of the binding interaction was calculated from the gel shift assay.

FIG. 12A: Binding affinity assay. Cy3-labeled RNAs were tested for binding to CHO-gp160 cells and CHO-EE control cells. Cell surface bindings of Cy3-labeled RNAs were assessed by flow cytometry. Aptamer 1 was one of reported gp120 aptamers. The 2$^{nd}$ RNA pool was a non-relevant RNA control. FIG. 12B: CHO-gp160 cells and CHO-EE control cells were grown on chamber slides and incubated with 40 nM of A-1 in culture medium for 2 hours. Cells were washed in PBS three times, fixed and stained with DIO (a plasma membrane dye), washed and analyzed by confocal microscopy.

FIG. 14A: The design of aptamer-siRNA chimeric RNAs. The region of anti-gp120 aptamer responsible for binding to gp120 (the A-1 aptamer or the B-68 aptamer) and the siRNA part of the chimera consists of 27 bps as an example here, targeting Site-I of HIV-1 tat/rev. FIG. 14B: The aptamer-siRNA chimeric RNAs that have comparable $K_d$ values specifically bind with $HIV_{Bal}$ gp120 protein as shown in this gel shift assay.

DETAILED DESCRIPTION OF THE INVENTION

Figure 1:
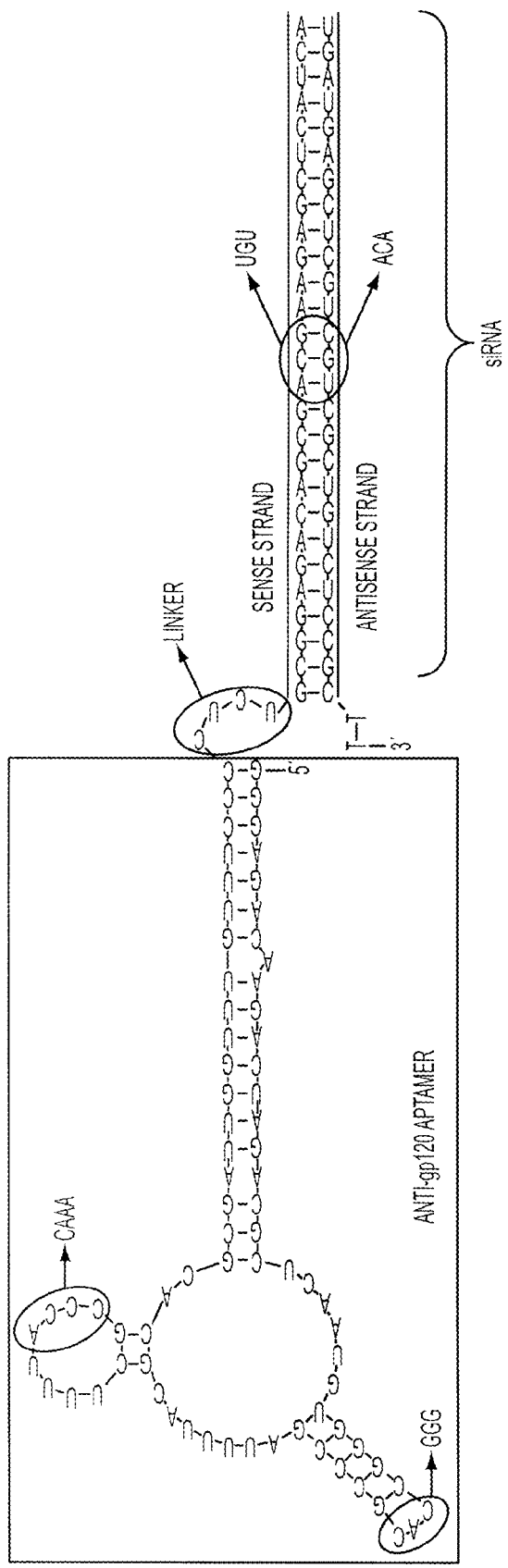
FIG. 1 shows the predicted secondary structure for anti-gp120 aptamer-siRNA chimeras. The sequence of the aptamer/linker/sense strand is SEQ ID NO:1, and the sequence of the antisense strand is SEQ ID NO:2. The region of anti-gp120 aptamer responsible for binding to gp120 is outlined in green. The siRNA part of the chimera consists of 27 bps as an example here, targeting Site-I of HIV-1 tat/rev. Two mutated chimeras M-1 (mutant aptamer) and M-2 (mutant siRNA) were constructed as experimental controls. Mutated regions are shown in magenta.

The present invention relates to compositions and methods for delivery of siRNA to specific cells or tissue. More particularly, the present invention relates to compositions and methods for cell type-specific delivery of anti-HIV siRNAs via fusion to an anti-gp120 aptamer.

In accordance with the present invention, we demonstrate cell type-specific delivery of anti-HIV siRNAs via fusion to an anti-gp120 aptamer. The envelope glycoprotein is expressed on the surface of HIV-1 infected cells, allowing binding and internalization of the aptamer-siRNA chimeric molecules. We demonstrate that the anti-gp120 aptamer-siRNA chimera is specifically taken up by cells expressing HIV-1 gp120, and the appended siRNA is processed by Dicer, releasing an anti-tat/rev siRNA which in turn inhibits HIV replication. We show for the first time a dual functioning aptamer-siRNA chimera in which both the aptamer and the siRNA portions have potent anti-HIV activities and that gp120 expressed on the surface of HIV infected cells can be used for aptamer mediated delivery of anti-HIV siRNAs.

In one aspect, the present invention provides a molecule for delivering siRNA to cells or tissues. In one embodiment, the molecule comprises the fusion of an aptamer that is specific for a cell or tissue with a siRNA to be delivered to the cell or tissue. In another embodiment, the aptamer is an anti-gp120 aptamer and the siRNA is directed against HIV-1. In a further embodiment, the siRNA is an anti-tat/rev siRNA. In one embodiment, the aptamer-sense strand siRNA is encoded by a DNA template. In another embodiment, the DNA template is transcribed to produce the aptamer-sense strand siRNA molecule. In a further embodiment, the aptamer-sense strand siRNA is annealed with an antisense strand siRNA to produce the aptamer-siRNA molecule. In one embodiment, pharmaceutical compositions comprising the aptamer-siRNA molecule are provided.

Thus, in accordance with the present invention, advantage of the gp120 glycoprotein (27, 28) binding properties of an anti-gp120 RNA aptamer was taken in order to explore the potential of using this aptamer for delivery of anti-HIV siRNAs into HIV infected cells. Based upon previous studies (29, 30), the aptamer as a chimeric transcript with a Dicer substrate RNA duplex (25-30 nt) was tested.

An "aptamer" refers to a nucleic acid molecule that is capable of binding to a particular molecule of interest with high affinity and specificity (41-42). The binding of a ligand to an aptamer, which is typically RNA, changes the conformation of the aptamer and the nucleic acid within which the aptamer is located. The conformation change inhibits translation of an mRNA in which the aptamer is located, for example, or otherwise interferes with the normal activity of the nucleic acid. Aptamers may also be composed of DNA or may comprise non-natural nucleotides and nucleotide analogs. An aptamer will most typically have been obtained by in vitro selection for binding of a target molecule. However, in vivo selection of an aptamer is also possible. An aptamer will typically be between about 10 and about 300 nucleotides in length. More commonly, an aptamer will be between about 30 and about 100 nucleotides in length. See, e.g., U.S. Pat. No. 6,949,379, incorporated herein by reference.

A Dicer substrate RNA duplex is a dsRNA that has been designed to be preferentially processed by the Dicer complex rather than feeding directly into the RISC complex. Such dsRNAs have been found to have enhanced potency/efficacy and duration of effect, as compared to corresponding siRNA agents. See, U.S. Patent Application Publication Nos. 2005/0244858, 2005/0277610 and 2007/0265220, each incorporated herein by reference, for descriptions of Dicer substrate RNA duplexes.

In accordance with the present invention, an anti-gp120 aptamer-siRNA chimera is prepared in which one strand of a 27 mer siRNA is covalently attached to the aptamer, and the second strand is base paired to the first strand. Similarly an anti-gp120 aptamer-siRNA chimera is prepared in which one strand of a 21 mer siRNA is covalently attached to the aptamer, and the second strand is base paired to the first strand. These chimeras were used to compare the use of a siRNA based on a 27 base pair dsRNA with the use of an siRNA based on a 21 base pair dsRNA. The anti-gp120 aptamer binding to the R5 version of HIV-1 gp120 has been previously demonstrated (31). This aptamer was shown to neutralize HIV-1 infectivity (31-33) by direct binding to gp120 in virions. It was desired to determine whether or not the anti-gp120 aptamer could provide selective binding and subsequent internalization into HIV infected cells which should express gp120 on the cell surface. Although the aptamer alone provided some inhibitory function when tested in this setting, the siRNA chimeras provided more potent inhibition than the aptamer alone, suggesting cooperativity between the siRNA and aptamer portions in inhibiting HIV replication and spread. The results described herein demonstrate that the gp120 aptamer-siRNA chimeras are internalized in cells expressing gp120 either ectopically or from HIV infection, and moreover the chimeric RNAs provide potent and lasting inhibition of HIV replication in T-cells in culture. These results support the concept of using aptamer-siRNA conjugates for systemic treatment of HIV infection. This approach has the major advantage of not relying upon gene therapy, and the siRNAs can be changed or multiplexed to avert viral resistance.

The aptamer-siRNA can also be designed to be more efficiently processed by Dicer. According to this embodiment, the dsRNA has a length sufficient such that it is processed by Dicer to produce an aptamer-siRNA and at least one of the following properties: (i) the dsRNA is asymmetric, e.g., has a 3' overhang on the sense strand and (ii) the dsRNA has a modified 3' end on the antisense strand to direct orientation of Dicer binding and processing of the dsRNA to an active siRNA. According to this embodiment, the longest strand in the dsRNA comprises 24-30 nucleotides. In one embodiment, the sense strand comprises 24-30 nucleotides and the antisense strand comprises 22-28 nucleotides. Thus, the resulting dsRNA has an overhang on the 3' end of the sense strand. The overhang is 1-3 nucleotides, such as 2 nucleotides. The antisense strand may also have a 5' phosphate. See, e.g., U.S. Patent Application Publication Nos. 2005/0244858, 2005/0277610 and 2007/0265220 for the design of dsRNA molecules that are more efficiently processed by Dicer.

In addition to the modifications discussed above, additional modifications can be made to the aptamer-siRNA molecule. Modifications can be included in the dsRNA, i.e., the aptamer-siRNA molecule, so long as the modification does not prevent the dsRNA composition from serving as a substrate for Dicer. In one embodiment, one or more modifications are made that enhance Dicer processing of the dsRNA. In a second embodiment, one or more modifications are made that result in more effective RNAi generation. In a third embodiment, one or more modifications are made that support a greater RNAi effect. In a fourth embodiment, one or more modifications are made that result in greater potency per each dsRNA molecule to be delivered to the cell. Modifications can be incorporated in the 3'-terminal region, the 5'-terminal region, in both the 3'-terminal and 5'-terminal region or in some instances in various positions within the sequence. With the restrictions noted above in mind any number and combination of modifications can be incorporated into the dsRNA. Where multiple modifications are present, they may be the same or different. Modifications to bases, sugar moieties, the phosphate backbone, and their combinations are contemplated. Either 5'-terminus can be phosphorylated.

In another embodiment, the antisense strand is modified for Dicer processing by suitable modifiers located at the 3' end of the antisense strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is an asymmetric composition with DNA on the blunt end and RNA bases on the overhanging end.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al. (51)). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988 and 6,291,438 and in U.S. published patent application No. 2004/0203145 A1, each incorporated herein by reference. Other modifications are disclosed in Herdewijn (52), Eckstein (53), Rusckowski et al. (54), Stein et al. (55) and Vorobjev et al. (56), each incorporated herein by reference.

Additionally, the aptamer-siRNA structure can be optimized to ensure that the oligonucleotide segment generated from Dicer's cleavage will be the portion of the oligonucleotide that is most effective in inhibiting gene expression. For example, in one embodiment of the invention a 27-bp oligonucleotide of the dsRNA structure is synthesized wherein the anticipated 21 to 22-bp segment that will inhibit gene expression is located on the 3'-end of the antisense strand. The remaining bases located on the 5'-end of the antisense strand will be cleaved by Dicer and will be discarded. This cleaved portion can be homologous (i.e., based on the sequence of the target sequence) or non-homologous and added to extend the nucleic acid strand.

In addition, the aptamer and the aptamer-siRNA chimera can be modified so that they contain 2'F-CTP and 2'F-UTP nucleotides to produce RNA that is resistant to RNase A degradation. Such modified RNA molecules are made using conventional techniques well known to the skilled artisan.

RNA may be produced enzymatically or by partial/total organic synthesis, and modified ribonucleotides can be introduced by in vitro enzymatic or organic synthesis. In one embodiment, each strand is prepared chemically. Methods of synthesizing RNA molecules are known in the art.

In a second aspect, the present invention provides a method for delivery of siRNA to specific cells or tissue. In one embodiment, the method comprises administering a pharmaceutical composition comprising a molecule for delivering siRNA to cells or tissues. In one embodiment, the molecule comprises the fusion of an aptamer that is specific for a cell or tissue with a siRNA to be delivered to the cell or tissue. In another embodiment, the aptamer is an anti-gp120 aptamer and the siRNA is directed against HIV-1. In a further embodiment, the siRNA is an anti-tat/rev siRNA. In another embodiment, the anti-gp120 aptamer-siRNA is delivered to HIV infected cells.

The aptamer-siRNA molecule can be suitably formulated and introduced into the environment of the cell by any means that allows for a sufficient portion of the sample to enter the cell to induce gene silencing, if it is to occur. Many formulations for dsRNA are known in the art and can be used. See, e.g., U.S. published patent application Nos. 2004/0203145 A1 and 2005/0054598 A1, each incorporated herein by reference. For example, siRNA can be formulated in buffer solutions such as phosphate buffered saline solutions, liposomes, micellar structures, and capsids. Formulations of siRNA with cationic lipids can be used to facilitate transfection of the dsRNA into cells. For example, cationic lipids, such as lipofectin (U.S. Pat. No. 5,705,188, incorporated herein by reference), cationic glycerol derivatives, and polycationic molecules, such as polylysine (published PCT International Application WO 97/30731, incorporated herein by reference), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

It can be appreciated that the method of introducing an aptamer-siRNA molecule into the environment of the cell will depend on the type of cell and the make up of its environment. For example, when the cells are found within a liquid, one preferable formulation is with a lipid formulation such as in lipofectamine and the aptamer-siRNA can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate aptamer-siRNA in a buffer or saline solution and directly inject the formulated dsRNA into cells, as in studies with oocytes. The direct injection of dsRNA duplexes may also be done. For suitable methods of introducing siRNA see U.S. published patent application No. 2004/0203145 A1, incorporated herein by reference.

Suitable amounts of aptamer-siRNA must be introduced and these amounts can be empirically determined using standard methods. Typically, effective concentrations of individual aptamer-siRNA species in the environment of a cell will be about 50 nanomolar or less 10 nanomolar or less, or compositions in which concentrations of about 1 nanomolar or less can be used. In other embodiment, methods utilize a concentration of about 200 picomolar or less and even a concentration of about 50 picomolar or less can be used in many circumstances.

The method can be carried out by addition of the aptamer-siRNA compositions to any extracellular matrix in which cells can live provided that the aptamer-siRNA composition is formulated so that a sufficient amount of the aptamer-siRNA can enter the cell to exert its effect. For example, the method is amenable for use with cells present in a liquid such as a liquid culture or cell growth media, in tissue explants, or in whole organisms, including animals, such as mammals and especially humans.

Expression of a target gene can be determined by any suitable method now known in the art or that is later developed. It can be appreciated that the method used to measure the expression of a target gene will depend upon the nature of the target gene. For example, when the target gene encodes a protein the term "expression" can refer to a protein or transcript derived from the gene. In such instances the expression of a target gene can be determined by measuring the amount of mRNA corresponding to the target gene or by measuring the amount of that protein. Protein can be measured in protein assays such as by staining or immunoblotting or, if the protein catalyzes a reaction that can be measured, by measuring reaction rates. All such methods are known in the art and can be used. Where the gene product is an RNA species expression can be measured by determining the amount of RNA corresponding to the gene product. The measurements can be made on cells, cell extracts, tissues, tissue extracts or any other suitable source material.

The determination of whether the expression of a target gene has been reduced can be by any suitable method that can reliably detect changes in gene expression. Typically, the determination is made by introducing the aptamer-siRNA into the environment of a cell such that at least a portion of that aptamer-siRNA enters the cytoplasm and then measuring the expression of the target gene. The same measurement is made on identical untreated cells and the results obtained from each measurement are compared.

The aptamer-siRNA can be formulated as a pharmaceutical composition which comprises a pharmacologically effective amount of an aptamer-siRNA and pharmaceutically acceptable carrier. A pharmacologically or therapeutically effective amount refers to that amount of an aptamer-siRNA effective to produce the intended pharmacological, therapeutic or preventive result. The phrases "pharmacologically effective amount" and "therapeutically effective amount" or simply "effective amount" refer to that amount of a RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA composition may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general a suitable dosage unit of aptamer-siRNA will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the aptamer-siRNA can be administered once daily. However, the therapeutic agent may also be dosed in dosage units containing two, three, four, five, six or more sub-doses administered at appropriate intervals throughout the day. In that case, the aptamer-siRNA contained in each sub-dose must be correspondingly smaller in order to achieve the total daily dosage unit. The dosage unit can also be compounded for a single dose over several days, e.g., using a conventional sustained release formulation which provides sustained and consistent release of the aptamer-siRNA over a several day period. Sustained release formulations are well known in the art. In this embodiment, the dosage unit contains a corresponding multiple of the daily dose. Regardless of the formulation, the pharmaceutical composition must contain aptamer-siRNA in a quantity sufficient to inhibit expression of the target gene in the animal or human being treated. The composition can be compounded in such a way that the sum of the multiple units of aptamer-siRNA together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al, *Current Protocols in Molecular Biology* (John Wiley & Sons, including periodic updates, 2008); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods For Examples 2-7

Materials: Unless otherwise noted, all chemicals were purchased from Sigma-Aldrich, all restriction enzymes were obtained from New England BioLabs (NEB) and all cell culture products were purchased from GIBOC (Gibco BRL/Life Technologies, a division of Invitrogen.).

siRNAs: siRNA and antisense strand RNA were purchased from Integrated DNA Technologies (IDT). Anti-tat/rev 27 mer siRNA: Sense sequence: 5'-GCGGAGACAGCGAC GAAGAGCUCAUCA-3' (SEQ ID NO:10); Antisense: 5'-UGAUGAGCUCUUCGUCGUG UCUCCGCdTdT-3' (SEQ ID NO:2); Anti-tat/rev 21 mer siRNA: Sense sequence: 5'-GCGG AGACAGCGACGAAGAGC-3' (SEQ ID NO:11); Antisense: 5'-GCUCUUCGUCGCUGUC UCCGCdTdT-3' (SEQ ID NO:3).

Aptamer-siRNA chimeras: The 27 or 21 mer sense strand is marked in bold, the linker (CUCU) is indicated in italics and mutated nucleotides are underlined. Aptamer: 5'-GG GAGA-CAAGACUAGACGCUCAAUGUGGGC-CACGCCCGAUUUUACGCUUUUACCCGC ACGCGA-UUGGUUUGUUUCCC-3' (SEQ ID NO:12). Ch L-1 sense strand: 5'-GGGAGAC AAGACUAGACGCUCAAU-GUGGGCCACGCCCGAUUUUACGCU-UUUACCCGCACGCG AUUGGUUUGUUUCCCCU-CUGCGGAGACAGCGACGAAGAGCUCAUCA-3' (SEQ ID NO:1). Ch 1 sense strand: 5'-GGGAGACAAGACUA-GACGCUCAAUGUGGGCCACGCC CGAUU-UUACGCUUUUACCCGCACGCGAUUGGU-UUGUUUCCCGCGGAGACAGCGA CGAAGAGCUCAUCA-3' (SEQ ID NO:13). Ch L-2 sense strand: 5'-GGGAGACAAGAC UAGACGCUCAAU-GUGGGCCACGCCCGAUUUUACGCU-UUUACCCGCACGCGAUUGG UUUGUUUCCCCU-CUGCGGAGACAGCGACGAAGAGC-3' (SEQ ID NO:14). Ch 2 sense strand: 5'-GGGAGACAAGACUA-GACGCUCAAUGUGGGCCACGCCCGAUUUUA CGCUUUUACCCGCACGCGAUUGGUUUGU-UUCCCGCGGAGACAGCGACGAAGAG C-3' (SEQ ID NO:15). M-1 sense strand: 5'-GGGAGACAAGACUA-GACGCUCAAUGU GGGCGGGGCCCGAUUUUAC CGUUUU<u>CA</u>AAGCACGCGAUUGGUUUGUUUCCCUC UGCG-<u>GAGA</u>CAGCGACGAAGAGCUCAUCA-3' (SEQ ID NO:16). M-2 sense strand: 5'-GGGAGACAAGACUA-GACGCUCAAUGUGGGCCACGCCCGAUU-UUACGCUUUUACC CGCACGCGAUUGGUUUGU-UUCCCCUCUGCGGAGACAGCG UGUAAGAGCUCAUC A-3' (SEQ ID NO:17). Ch L-1, Chl and M-1 antisense strand: 5'-UGAUGAGCUCUU CGUCGCUGUCUCCGCdTdT-3' (SEQ ID NO:2). Ch L-2, Ch 2 antisense strand: 5'-GCUCU UCGUCGCUGUCUC- CGCdTdT-3' (SEQ ID NO:3). M-2 antisense strand: 5'-UGAUGAG CUCUUACACGCUGUCUCCGCdTdT-3' (SEQ ID NO: 18).

Generation of aptamer and chimera RNAs by in vitro transcription: Double-stranded DNA templates were directly generated by PCR and the resulting PCR products were recovered using a QIAquick Gel purification Kit. Chimera sense strands were transcribed from its PCR generated DNA templates using the DuraScription Kit (Epicentre, Madison, Wis.) according to the manufacturer's instruction. In the transcription reaction mixture, the canonical CTP and UTP were replaced with 2'-F-CTP and 2'-F-UTP to produce RNA that is resistant to RNase A degradation. The reactions were incubated at 37° C. for 6 h, and subsequently purified with Bio-Spin 30 Columns (Bio-Rad) following phenol extraction and ethanol precipitation. RNA was treated by CIP to remove the initiating 5'-triphosphate. To prepare the chimeras, the chimeras harboring only the sense strand RNA was combined with the appropriate antisense RNA in HBS buffer (10 mM HEPES pH 7.4, 150 mM NaCl, 1 mM $CaCl_2$, 1 mM $MgCl_2$, 2.7 mM KCl), heated to 95° C. for 3 min and then cooled to 37° C. slowly. Incubation continued at 37° C. for 10 min. Fluorescent aptamer and chimeras were generated using the Silencer siRNA Labeling Kit (Ambio) according to the manufacturer's instructions.

Cell Culture: HEK 293 cells and CEM cells were purchased from ATCC and cultured in DMEM and RPMI 1640 supplemented with 10% FBS respectively, according to their respective data sheets. CHO-WT and CHO-EE cells were obtained through the AIDS Research and Reference Reagent Program, Division of AIDS, NIAID, NIH. They are grown in GMEM-S. Cells were cultured in a humidified 5% $CO_2$ incubator at 37° C.

Cell-surface binding of aptamer-siRNA chimeras (flow cytometry analysis): CHO-gp160 or CHO-EE cells were washed with PBS, trypsinized and detached from the plates. After washing cells twice times with 500 μL of binding buffer (10 mM HEPES pH 7.4, 150 mM NaCl, 1 mM $CaCl_2$, 1 mM $MgCl_2$, 2.7 mM KCl, 0.01% BSA). Cell pellets were resuspended in binding buffer and incubated at 37° C. for 30 min. Cells were then pelleted and resuspended in 50 μL of binding buffer (prewarmed to 37° C.) containing either 400 nM Cy3-labeled aptamer or Chimera RNAs. After incubation at 37° C. for 40 min, cells were washed three times with 500 μL of binding buffer prewarmed to 37° C., and finally resuspended in 350 μL of binding buffer prewarmed to 37° C. and analyzed by flow cytometry.

Cellular binding and uptake studies (confocal microscopy analysis): The CHO-gp160 and CHO-EE cells lines were grown in 8-well chambered-slide with seeding at $1 \times 10^5$ in GMEM-S medium to allow 50%-70% confluence in 24 h. On the day of experiments, cells were washed with 250 μL of prewarmed PBS. And incubated with 250 μL of prewarmed completely growth medium for 30 min at 37° C. Cy3-labeled RNAs at 20 nM of final concentration were added into the media and incubated at 37° C. for 1.5 hrs. Subsequently, cells were washed three times with 250 μL of prewarmed PBS, fixed with 4% formaldehydes for 10 min. The cells were stained by treatment with 100 μL of Vybrant Cell-Labeling Solution (DIO membrane dye, Molecular Probes, Invitrogen) according to the manufacturer's instructions. The images were collected using a Zeiss LSM 510 upright 2 photon confocal microscopy system under water immersion at 40 magnifications. Images were combined and deconvoluted to reconstruct a three-dimensional image.

Analysis of chimera processing: Sense RNAs were annealed with equal moles of 5'-end-labeled antisense strands in HBS buffer in order to form chimeric dsRNA. The chimeras or dsRNAs were incubated at 10 nM of final concentration in the absence of target mRNA in HCT116 cell lysates for varying times (20 min, 60 min and 120 min). Reactions were stopped by phenol/chloroform extraction and the RNAs were collected for electrophoresis in a denaturing 20% polyacrylamide gel. The gels were subsequently dried and exposed to X-ray film.

Dual luciferase assays: (Day 1) CHO-gp160 and CHO-EE cells were transfected with pNL4-3. Luc.R-.E- (NIH AIDS Research and Reagent Program, Germantown, Md.) and pRSV-*Renilla* using Lipofectamine 2000 (Invitrogen) according to the manufacturer's instructions. pNL4-3. Luc.R-.E- is an Env-Vpr-non-infectious clone containing the firefly luciferase (F-Luc) gene inserted into the nef gene. (Day 2) Cells which transiently expressed pNL4-3.Luc were seeded in 24-well plates at 50-70% confluency. For siRNA, (Day 3) cells were transfected with 200 nM RNA using Lipofectamine 2000. For aptamer-mediated siRNA delivery, (Day 3) cells were incubated in 400 μL refresh complete growth media for 30 min at 37° C. The chimeras RNAs were added directly to the media (400 μL) at a final concentration of 200 nM chimeras. Cells were harvested for analysis on day 4. The expression of the pNL4-3.Luc and normalizing control *Renilla* luciferase were detected by the Dual-luciferase Reporter Assay System (Promega, USA) according to the manufacturer's instructions. All samples were transfected in triplicate and the experiment was performed a minimum of three times.

5'-ACE PCR assay: Total RNA (5 g) from CHO-gp160 cells treated with different siRNAs and chimeras was ligated to a GeneRacer adaptor (Invitrogen) without prior treatment. Ligated RNA was reversed transcribed using a gene specific primer 1 (GSP-Rev 1: 5'-TCACCCTCTCCACTGACA-GAGAACTT-3' (SEQ ID NO:19)). To detect cleavage products, PCR was preformed using primers complementary to the RNA adaptor (5'-cDNA primer: 5'-GGACACTGA-CATGGACTGAAGGAGTA-3' (SEQ ID NO:20)) and gene-specific primer 2 (GSP-Rev 2: 5'-TAACCTCTCAAGCG-GTGGTAGCTGAA-3' (SEQ ID NO:21)). Amplification products were resolved by agarose gel electrophoresis and visualized by ethidium bromide staining. The identity of the specific PCR products was confirmed by sequencing of the excised bands.

Northern blot analysis: CEM cells were infected by HIV NL4-3 for 10 days. Prior to adding the various RNAs, the infected-CEM cells were gently washed 3 times to clear out free virus. $5 \times 10^4$ cells were incubated with refolded RNAs at 400 nM final concentrations in 96-well plates at 37° C. The total RNAs were harvested on the 7th day post application for analysis with STAT-60 (TEL-TEST "B", Friendswood, Tex.) according to the manufacturer's instructions. Two micrograms of total RNAs were electrophoresed in a 15% polyacrylamide-8 M urea gel and then transferred to a Hybond N+ membrane (Amersham pharmacia Biotech, USA). Prehybridization and hybridization were carried out using PerfectHyb Plus Hybridization buffer (Sigma, USA) at 37° C. with 3 pmol of a 27-mer DNA oligonucleotide probe end-labeled with T4 polynucleotide kinase and $\gamma$-$P^{32}$-ATP. Filters were washed three times at 37° C. for 15 min, prior to autoradiography. We also probed for human U6 snRNA as an internal RNA loading standard.

qRT-PCR analysis: CEM cells were infected with HIV NL4-3 for 10 days. Prior to analyses, the infected-CEM cells were gently washed three times to eliminate free virus. The infected CEM cells were treated directly with the aptamer or Ch L-1 at 400 nM of final concentration. After 7 d, total RNAs were isolated with STAT-60 (TEL-TEST "B", Friendswood, Tex.). Expression of the tat/rev coding RNAs was analyzed by quantitative RT-PCR using 2× iQ SyberGreen Mastermix (BIO-RAD) and specific primer sets at a final concentration of 400 nM. Primers were as follows: tat/rev forward primer: 5'-GGCGTTACTC GACAGAGGAG-3' (SEQ ID NO:22); tat/rev reverse primer: 5'-TGCTTTGATAGAGAAGC TTGATG-3' (SEQ ID NO:23); GAPDH forward primer: 5'-CATTGACCTCAACTACATG-3' (SEQ ID NO:24); GAPDH reverse primer: 5'-TCTCCATGGTGGTGAAGAC-3' (SEQ ID NO:25).

RNA-Stat60 was used to extract total RNA according to the manufacturer's instruction (Tel-Test). Residual DNA was digested using the DNA-free kit per the manufacturer's instructions (Ambion). cDNA was produced using 2 μg of total RNA Moloney murine leukemia virus reverse transcriptase and random primers in a 15 μL reaction according to the manufacturer's instructions (Invitrogen). GAPDH expression was used for normalization of the qPCR data.

HIV-1 challenges and p24 antigen assay: Method 1: NL4-3 virus was incubated with refolded RNAs at 37° C. for 1 h. Subsequently, viruses were gently washed with PBS and used to infect CEM cells. The culture supernatants were collected at different time post infection (7 d, 11 d, 15 d and 18 d) for p24 antigen analyses. Method 2: CEM cells were infected with HIV NL4-3 for 10 days. Prior to RNA treatments the infected-CEM cells were gently washed with PBS three times to eliminate free virus. $1.5 \times 10^4$ infected CEM cells and $3.5 \times 10^4$ uninfected CEM cells were incubated with refolded RNAs at 400 nM of final concentration in 96-well plates at 37° C. The culture supernatants were collected at different time (3 d, 5 d, 7 d and 9 d). The p24 antigen analyses were performed using a Coulter HIV-1 p24 Antigen Assay (Beckman Coulter) according to the manufacturer's instructions.

Interferon assay (qRT-PCR Analysis): For HEK293 cells, the cells were transfected with siRNA and chimeras RNAs (50 nM) or 200 ng poly(IC) using lipofectamine 2000 (Invitrogene). For infected CEM cells, cells were directly treated with chimera RNAs (400 nM) or IFN-alpha (100 U/mL). After 24 h, total RNAs were isolated with STAT-60 (TEL-TEST "B", Friendswood, Tex.). Expression of human mRNAs encoding IFN-β, p56 (CDKL2) and OAS1 were analyzed by quantitative RT-PCR using 2× iQ SyberGreen Mastermix (BIO-RAD) as described above and specific primer sets for these genes at final concentrations of 400 nM. Primers were as follows: IFN-β forward, 5'-AGACTTACAG-GTTACCTCCGAA-3' (SEQ ID NO:26); IFN-β reverse, 5'-CAGTACATTCGCCATCAGTCA-3' (SEQ ID NO:27); P56 forward, 5'-GCCTCCTTGGGTTCGTCTATAA-3' (SEQ ID NO:28); P56 reverse, 5'-CTCAG GGCCCGCT-CATAGTA-3' (SEQ ID NO:29); OAS 1 forward, 5'-GGAG-GTTGCAGTGCC AACGAAG-3' (SEQ ID NO:30); OAS 1 reverse, 5'-TGGAAGGGAGGCAGGGCATAAC-3' (SEQ ID NO:31).

Example 2

Design of Anti-gp120 Aptamer-siRNA Chimeras

Anti-gp120 aptamer-siRNA chimeras were designed for cell-specific delivery and siRNA processing. To enhance the stability of the chimeric RNAs in cell culture and in vivo (4, 34-37), the aptamer and sense strand segment of the siRNAs contained nuclease-resistant 2'-Fluoro UTP and 2'-Fluoro CTP and were synthesized from corresponding dsDNA templates by in vitro bacteriophage transcription (FIG. 1). To prepare the siRNA containing chimeras, in vitro transcribed chimeric aptamer-sense strand polymers were annealed with equimolar concentrations of an unmodified antisense strand RNA. These 2'-Fluoro modified chimeras were stable in cell-culture media for up to 48 hours whereas the unmodified control RNAs were quickly degraded within several minutes (data not presented).

The gp120-binding aptamer which neutralizes R5 strains of HIV-1 has been previously described and characterized (31). Since the synthetic Dicer substrate duplexes of 25-30 nt have been shown to enhance RNAi potency and efficacy, we chose a 27 mer duplex RNA as the siRNA portion of our chimeric molecule. The 27 mer siRNA portion of chimeras (Ch L-1 and Ch 1) targets the HIV-1 tat/rev common exon sequence. The chimeras designed Ch L-2 and Ch 2 are identical to Ch L-1 and Ch 1 with the exception that the 27 mer duplex is replaced by a 21 base pair duplex. In the Ch L-1 and Ch L-2 designs we inserted a four nucleotide linker (CUCU) between the aptamer and siRNA portions to minimize steric interference of the aptamer portion with Dicer. Previous studies on the anti-gp120 aptamer identified the minimal region of the aptamer essential for binding gp120 and showed mutations within this region significantly lower the binding affinity. As controls for aptamer binding we created the chimera designated as M-1. As a control for the siRNA mediated silencing we constructed an additional mutant in the siRNA portion which should abrogate RNAi directed cleavage of the target, and this is designated as M-2.

Figure 7:
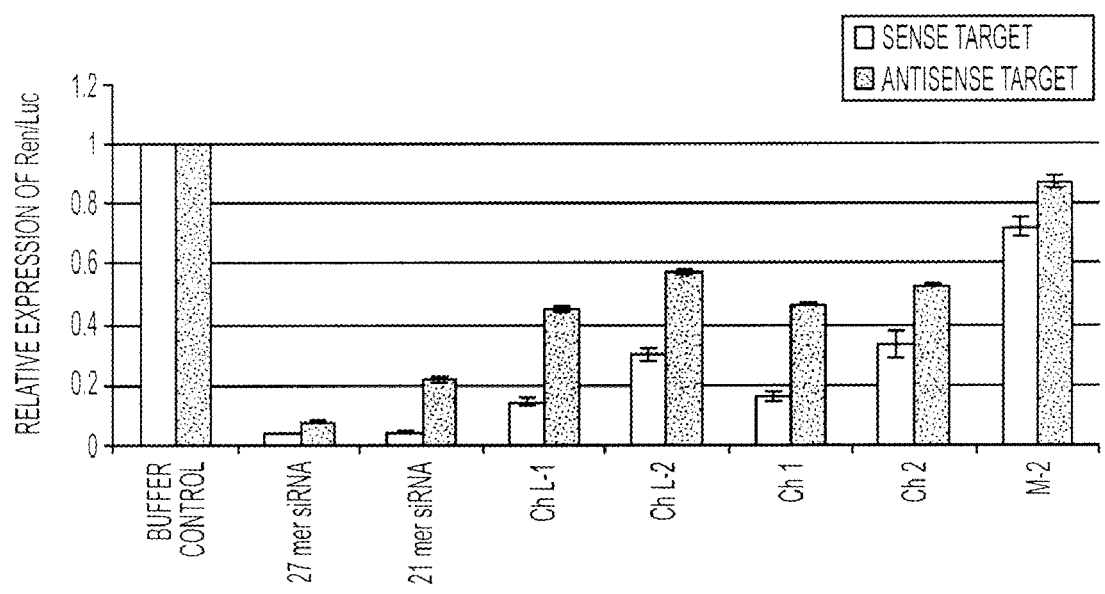
FIG. 7 shows the gene silencing activity and strand selectivity of chimeras RNAs and siRNA. Dual luciferase assays of psiCHECK sense and anti-sense targets are shown. All RNAs are normalized to the valued of the corresponding buffer control. The strand selectivity was calculated as: $R_{buffer}=1.0$; $R_{27mer\ siRNA}=2.2$; $R_{21mer\ siRNA}=4.9$; $R_{Ch\ L-1}=3.2$; $R_{Ch\ L-2}=1.9$; $R_{Ch\ 1}=2.9$; $R_{Ch\ 2}=1.6$; $R_{M-2}=1.2$, respectively.

Because of competition by the sense (passenger) strand with the anti-sense (guide) strand for RISC entry, the strand selectivity is an important factor for evaluating siRNAs. Therefore, we evaluated these chimeras RNA using the SiCheck reporter system, which readily allows screening of the potencies of candidate sh/siRNAs. The gene silencing of both the sense target (corresponding to the mRNA) and the anti-sense target were tested independently and the selectivity ratios could be calculated as a measure of the relative incorporation of each strand into the RISC. The comparison (FIG. 7) demonstrated that the Ch L-1 mediated ~86% knockdown of the sense target; however, knockdown of the anti-sense target is much less (~50%), indicative of good strand selection (R=3.2). Ch 1 also indicated similar knockdown (83%) of the sense target and strand selection (R=2.9). In contrast, Ch L-2 and Ch 2 have poorer efficacy (<70%) and strand selectivity (R=1.9 and 1.6, respectively). These data suggest that the aptamer-27 mer siRNA chimeras indeed enhance the RNAi efficacy and potent, consistent with previous studies in our laboratory (29, 30).

Example 3

Anti-gp120 Aptamer-siRNA Chimeras Bind and are Internalized by Cells Expressing HIV gp160

Figure 2A:
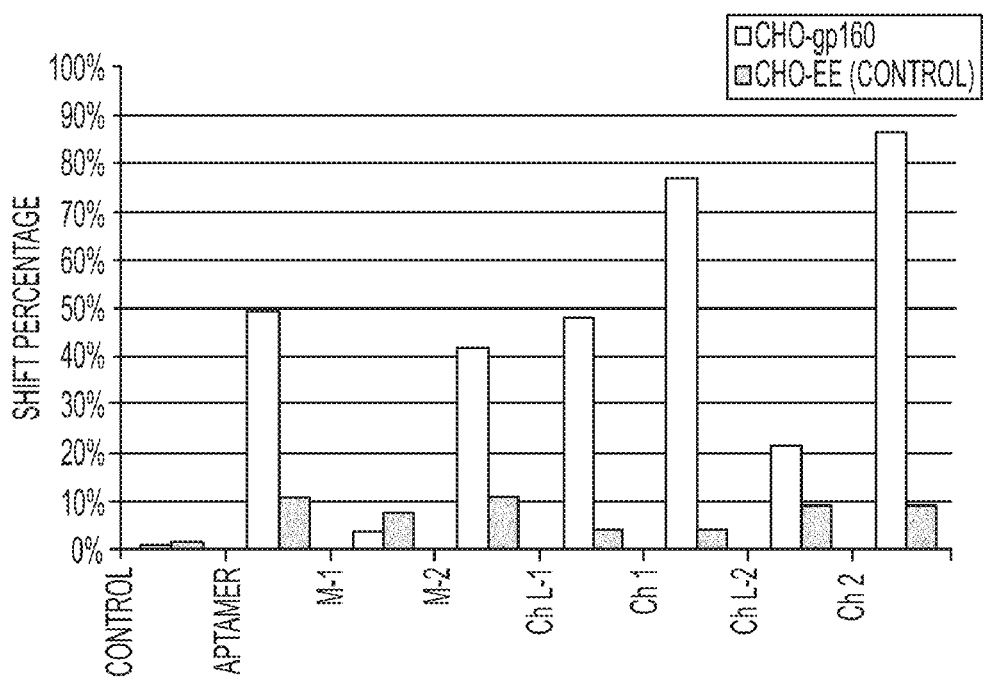
FIG. 2A shows a binding affinity assay. Cy3-labeled RNAs were tested for binding to CHO-gp160 cells and CHO-EE control cells. Cell surface binding of Cy3-labeled aptamer-siRNA chimeras were assessed by flow cytometry.

We found that anti-gp120 aptamer-siRNA chimeras bind and are internalized by cells expressing HIV gp160. CHO-gp160 cells stably expressing the HIV envelope glycoprotein gp160 were used to test uptake of the chimeric aptamer-siRNAs. These cells do not process gp160 into gp120 and gp41 since they lack the gag encoded proteases required for envelope processing. As a control we used the parental CHO-EE cell line which does not express gp160. The anti-gp120 aptamer and the chimeras were labeled with Cy3 to follow their binding and potential internalization in gp160 expressing cells. Flow cytometric analyses (FIG. 2A) revealed that the aptamer and chimeras specifically bound to the CHO-gp160 cells but did not bind to the control CHO-EE cells. As anticipated, the M-1 dramatically reduced binding to the CHO-gp160 expressing cells.

Figure 2B:
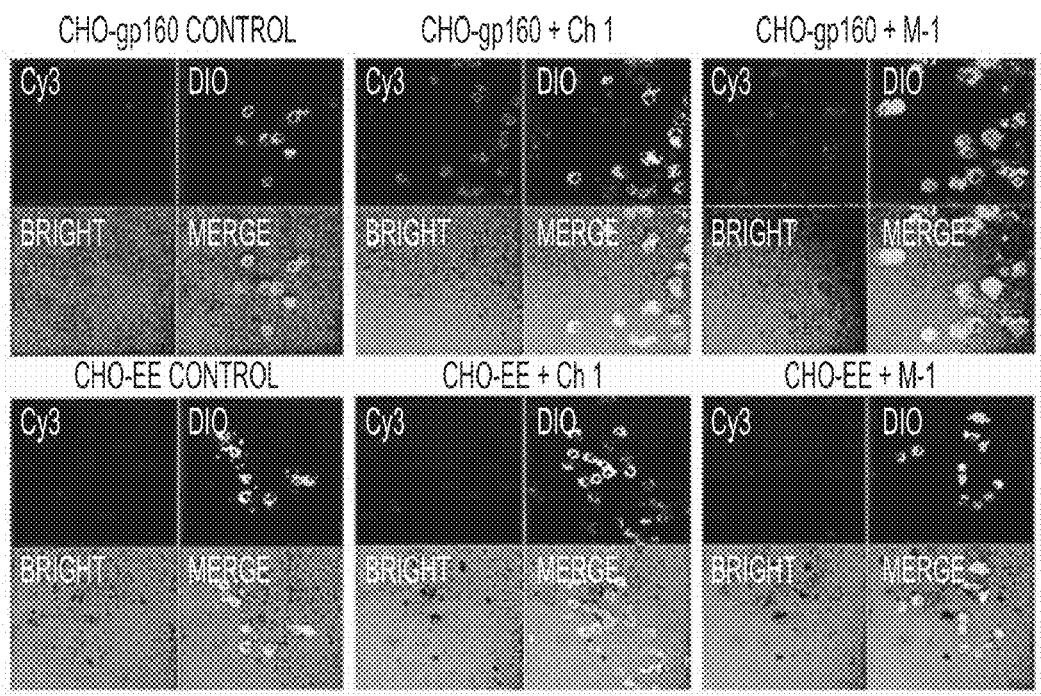
FIG. 2B shows the binding and uptake of Ch 1 to CHO-gp160 cells. CHO-gp160 cells and CHO-EE control cells were grown on chamber slides and incubated with 20 nM of Ch 1 in culture medium for 2 hours. Cells were washed in PBS three times, fixed and stained with DIO (a plasma membrane dye), washed and analyzed by confocal microscopy.
Figure 8:
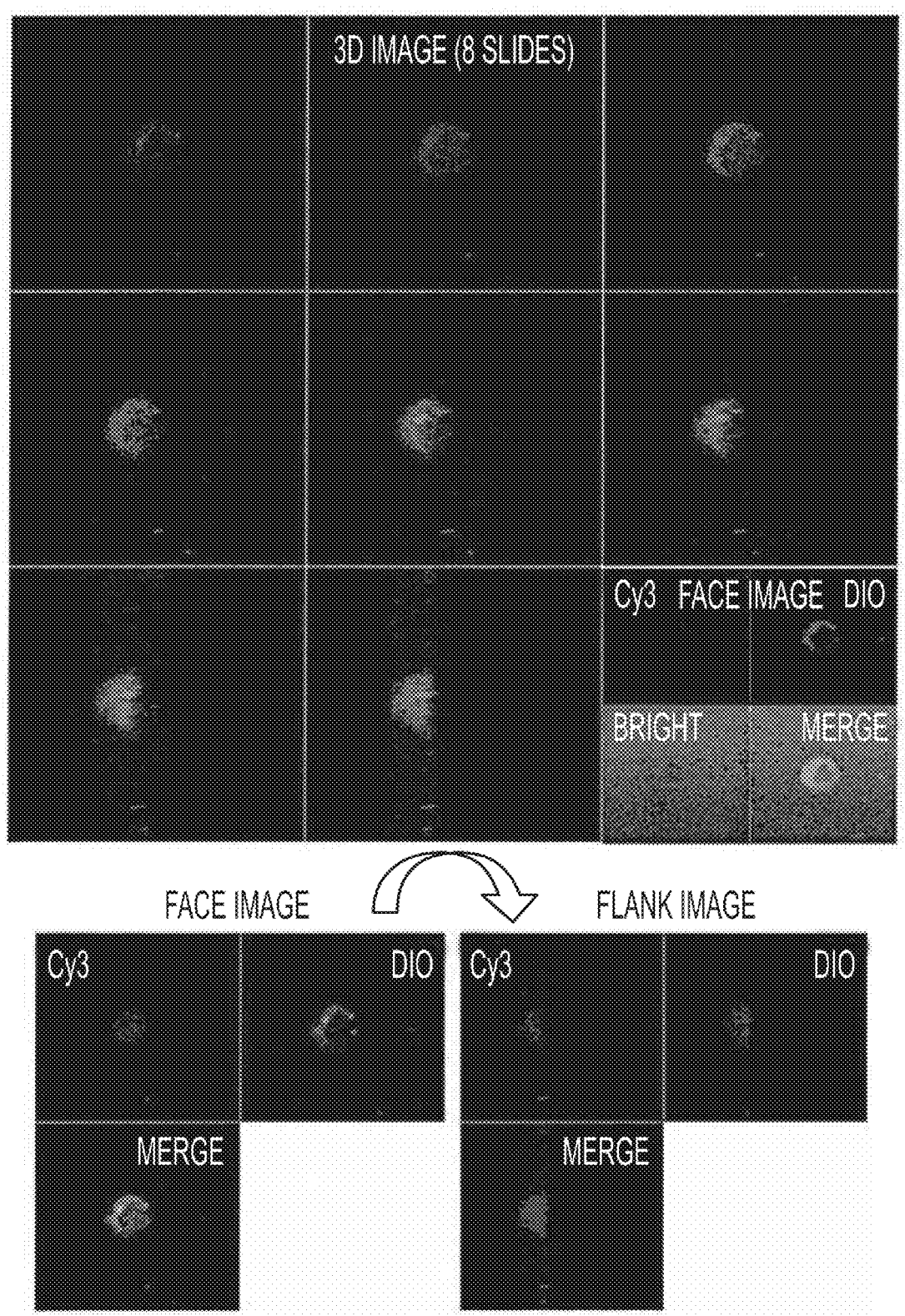
FIG. 8 shows that images were combined and deconvoluted to reconstruct a three-dimensional image. Three-dimensional image reconstruction shows localization of the Cy3-labeled Ch 1 in a single cell.

In order to determine if the bound aptamer and chimeras were internalized in the gp160 expressing cells, we carried out Z-axis confocal microscopy and three-dimensional image reconstruction with the CHO-gp160 cells incubated with the Cy3-labeled transcripts. Both the anti-gp120 aptamer (data not presented) and Ch 1 (FIG. 2B) were selectively internalized within the CHO-gp160 cells but not the CHO-EE control cells. The M-1 was also not internalized. Three-dimensional image reconstruction (FIG. 8) shows localization of the Cy3-labeled Ch 1 in a single cell. To visualize the plasma membranes the cells were stained with the carbocyanine dye DIO.

Example 4

Anti-gp120 Aptamer-siRNA Chimeras are Processed by Dicer

Figure 3A:
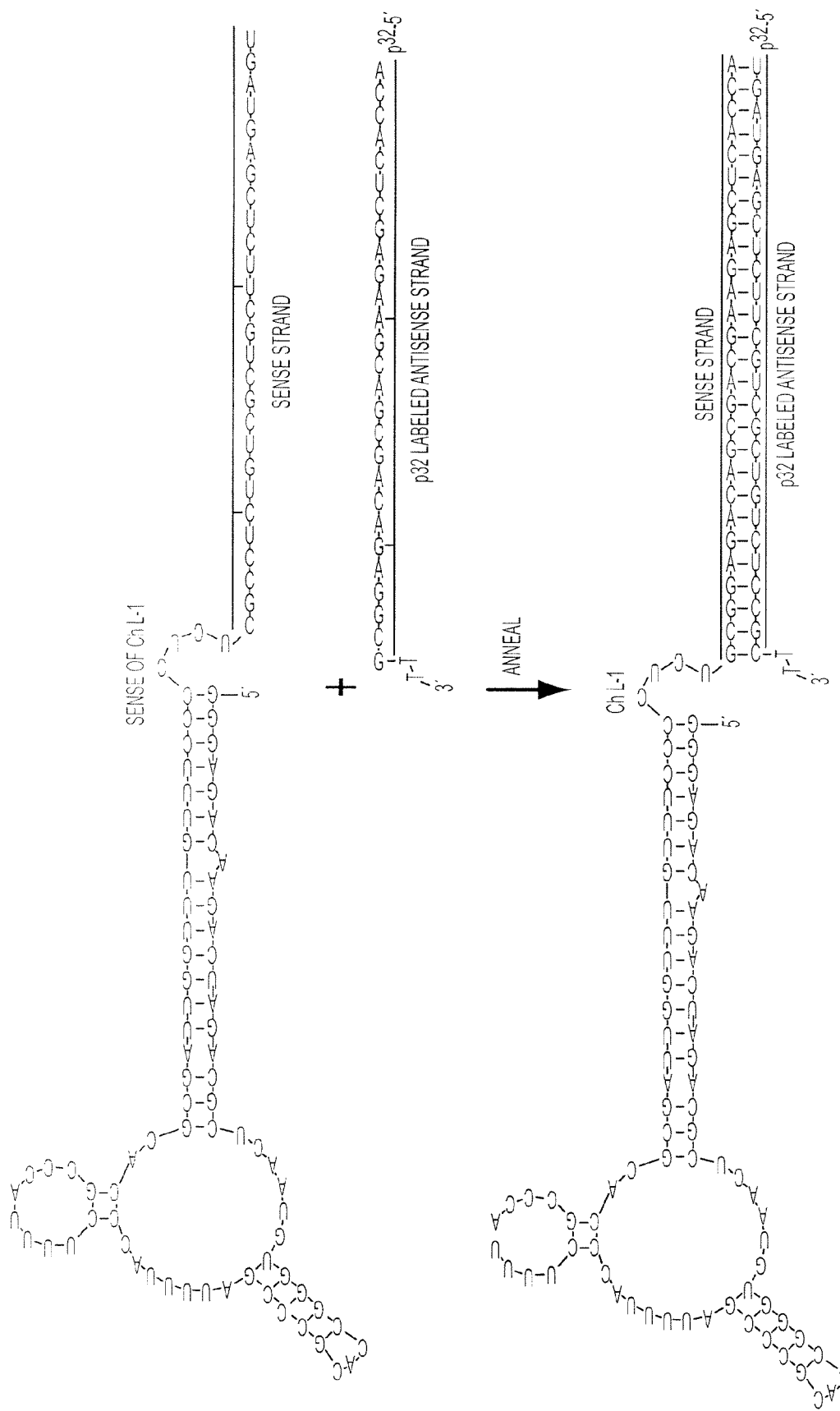
FIGS. 3A and 3B show the analysis of chimera processing. 21-23 nt RNA fragments are produced following incubation of chimera RNAs in HCT116 cell extracts.
Figure 3B:
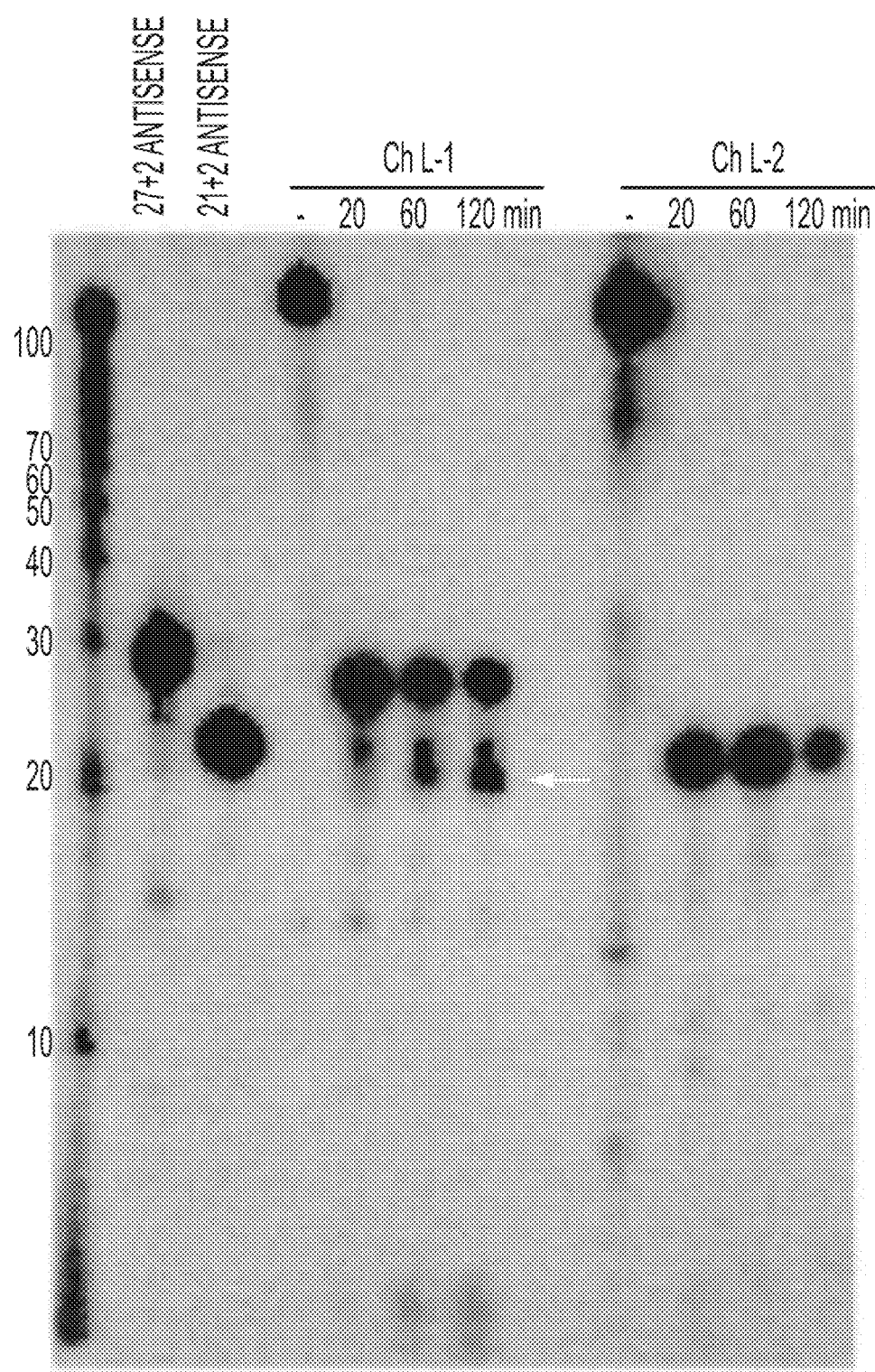

We next asked whether or not the siRNAs could be processed from the chimeras by Dicer in whole cell extracts that contain good Dicer cleavage activity. The first set of experiments used a 5'-end $P^{32}$ labeled antisense strand to follow Dicer processing (FIG. 3A). The size of the $P^{32}$ labeled cleavage product(s) indicates from which direction Dicer enters the siRNA and cleaves. When Ch L-1 was incubated with the cytoplasmic lysate, we observed that the 27 nt antisense strand was processed into a 21-23 nt siRNA (FIG. 3B). This result suggests Dicer processing preferentially enters from the 5' end of the antisense strand and cleaves 21 to 23 nt downstream, leaving the 5' end of the antisense strand intact. In contrast, the 21 base siRNAs were not processed further in these extracts.

Example 5

Anti-gp120 Aptamer-siRNA Chimeras Specifically Silence Target Gene Expression

To evaluate whether these anti-gp120 aptamer-siRNA chimeras function in triggering RNAi, we first transfected CHO-gp160 and CHO-EE cells with HIV pNL4-3 Luc. The HIV pNL4-3 has the firefly luciferase under the control of the HIV LTR and is Tat responsive. The anti-tat/rev siRNA efficacy is monitored by inhibition of luciferase expression. Subsequent to the transfections the cells were treated with the chimeras in the absence or presence of the transfection reagent Lipofectamine 2000.

Figure 4A:
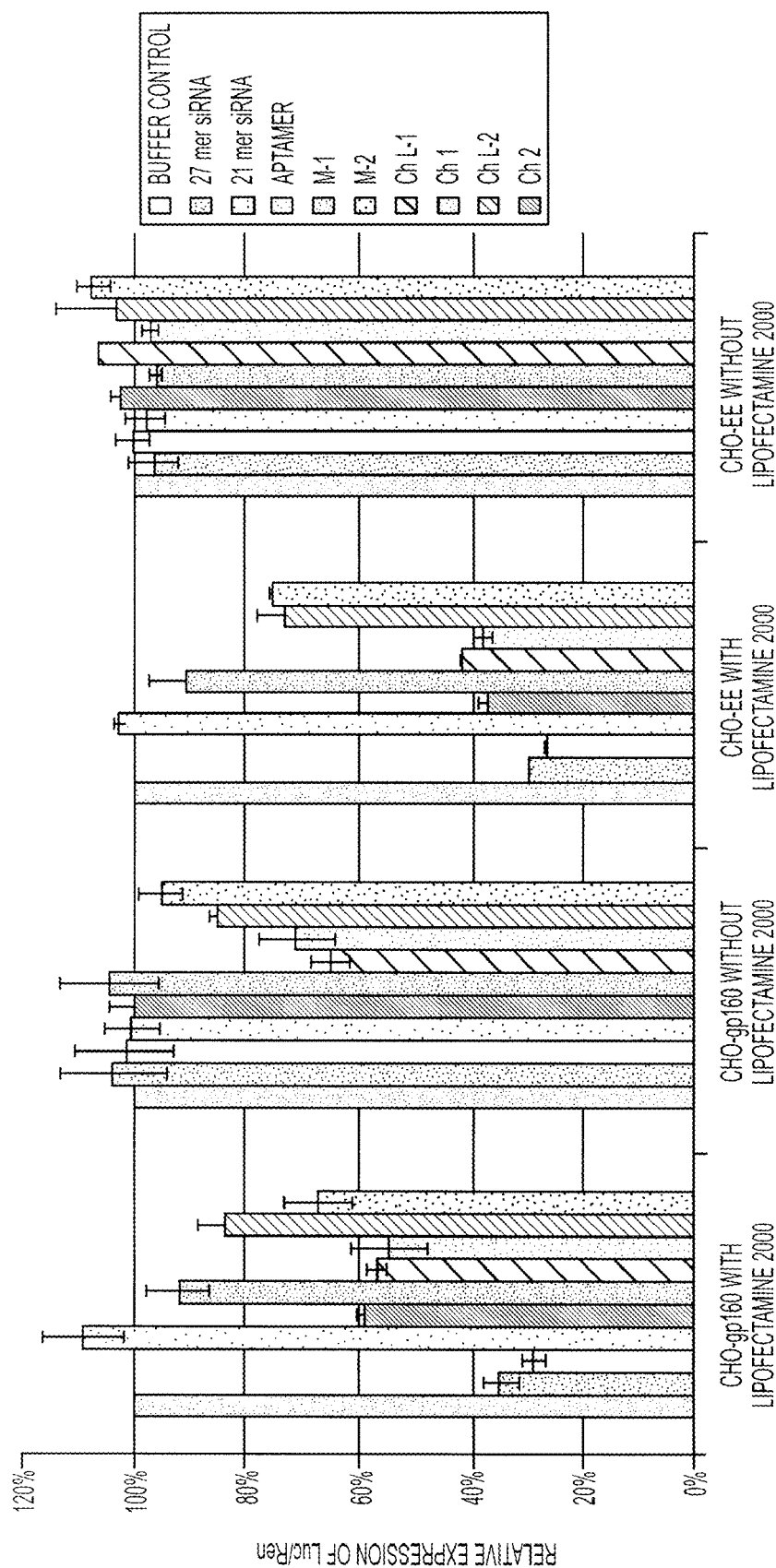
FIG. 4A shows that aptamer-siRNA chimeras-mediate silencing of pNL4-3 luciferase. CHO-gp160 cells or CHO-EE cells transfected with pNL4-3 luc were incubated with 200 nM of the experimental RNAs in the presence or absence of the transfection reagent lipofectamine 2000. In the absence of the transfection reagent inhibition of pNL4-3 luc expression was only observed for CHO-gp160 cells. These results are consistent with the aptamer mediated binding to gp160 and internalization of the chimera followed by processing into siRNAs. The data were normalized with *Renilla* luciferase expression and represent the average of three replicate assays.

Luciferase expression was potently inhibited when Ch L-1 and Ch 1 were lipofected into both types of cells (FIG. 4A). However, in the absence of lipofection, gene silencing from Ch L-1 and Ch 1 was specific to CHO-gp160 expressing cells and no inhibition of luciferase was observed in CHO-EE cells. Interestingly, Ch L-1 and Ch 1 which are linked to the 27 mer duplex RNA showed somewhat greater efficacy than Ch L-2 and Ch 2, consistent with our previous observations of Dicer substrates enhancing RNAi (29, 30).

Figure 4B:
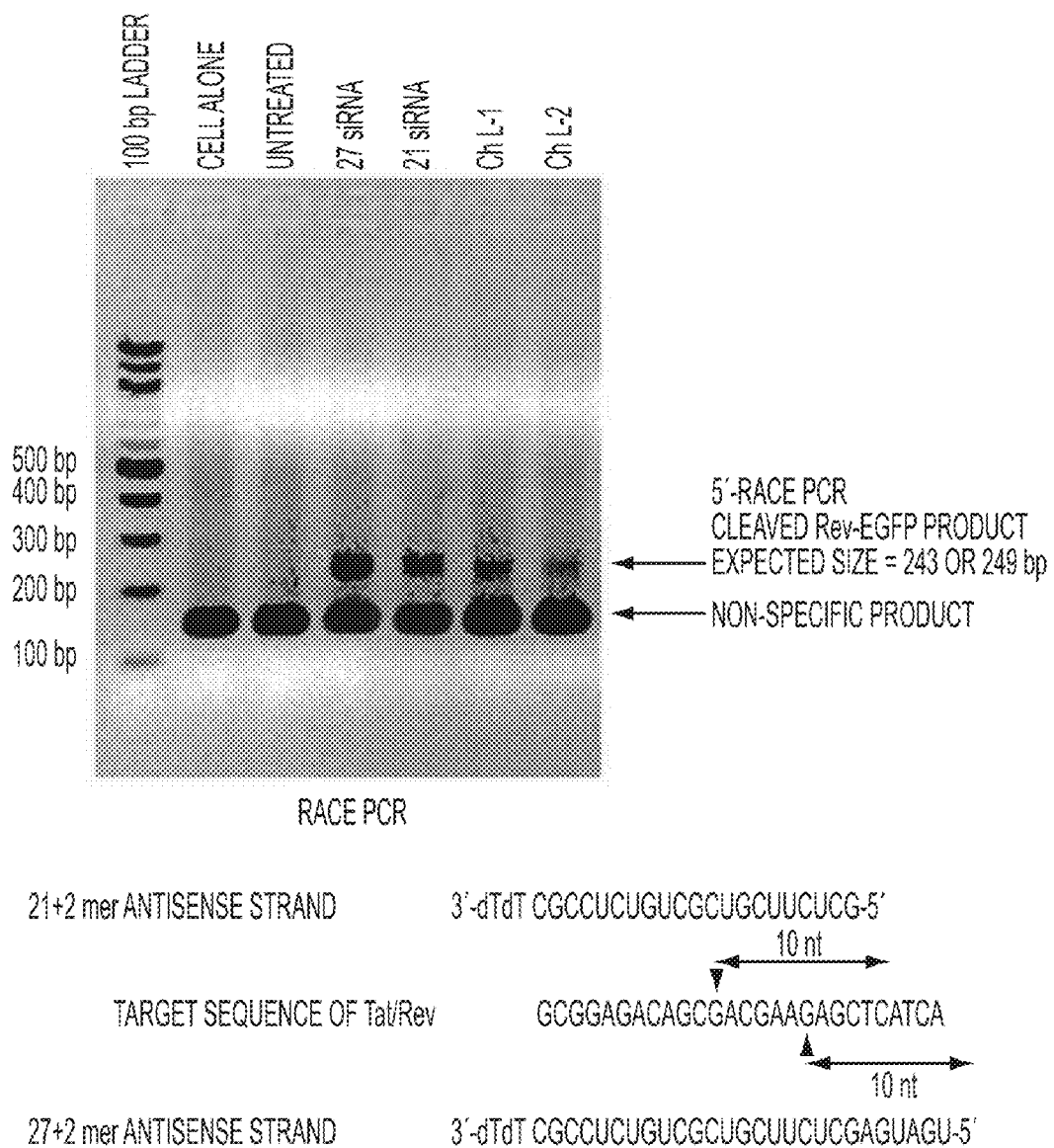
FIG. 4B shows that cleaved mRNA from CHO-gp160 cells previously transfected with either saline (untreated), Tat-Rev site 127-mer siRNA, 21-mer siRNA, Ch L-1 and Ch L-2 RNAs, was ligated to an RNA adaptor and reverse transcribed using a gene-specific primer. Depicted is an agarose gel electorphoresis of the 5'-RACE-PCR amplification products using a primer specific to the RNA adaptor and a reverse primer (GSP-Rev-2) to Rev-EGFP, indicated specific siRNA-mediated cleavage products of Rev-EGFP mRNA. The sequence of the "21+2 mer antisense strand" is SEQ ID NO:3. The sequence of the "Target sequence of Tat/Rev" is SEQ ID NO:4. The sequence of the "27+2 mer antisense strand" is SEQ ID NO:2.

To validate that the siRNAs released from the chimeras were triggering RNAi we transfected CHO-gp160 cells with a Rev-EGFP fusion construct harboring the siRNA targets. The transfected cells were then transfected with Ch L-1, Ch L-2, 27 mer siRNA or 21 mer siRNA in presence of Lipofectamine 2000. Thirty six hours post transfection total RNA was isolated and subjected to a modified 5'-RACE (Rapid amplification of cDNA ends) technique to identify the specific cleavage products in the Rev portion of the fusion transcript. We assumed that the Ago2 mediated cleavage was between bases 10 and 11 relative to the 5' end of each siRNA. Our Dicer analyses of the 27 mer revealed that it is cleaved 21-23 nucleotides downstream from the 5' end of the antisense strand (antisense relative to the tat/rev target), whereas the 21 mer is not processed further (FIG. 3B). We expected that the RNAi mediated cleavage site in the target would be shifted by six bases between the 27 mer and the 21 mer derived siRNAs. Fragments of the predicted lengths were obtained from cells treated with the siRNAs or chimeras (FIG. 4B). Direct sequencing of the excised bands verified the expected PCR product, which demonstrated that cleavage occurred at the predicted position for the siRNA duplex between positions 10 and 11 from the 5' end of the siRNA antisense strand (FIG. 9). These data provide a formal demonstration that the chimeras produce siRNAs that are incorporated into RISC. As expected, no RACE PCR products were generated from RNA isolated from cells untreated with the chimeras or siRNAs.

Example 6

Figure 5A:
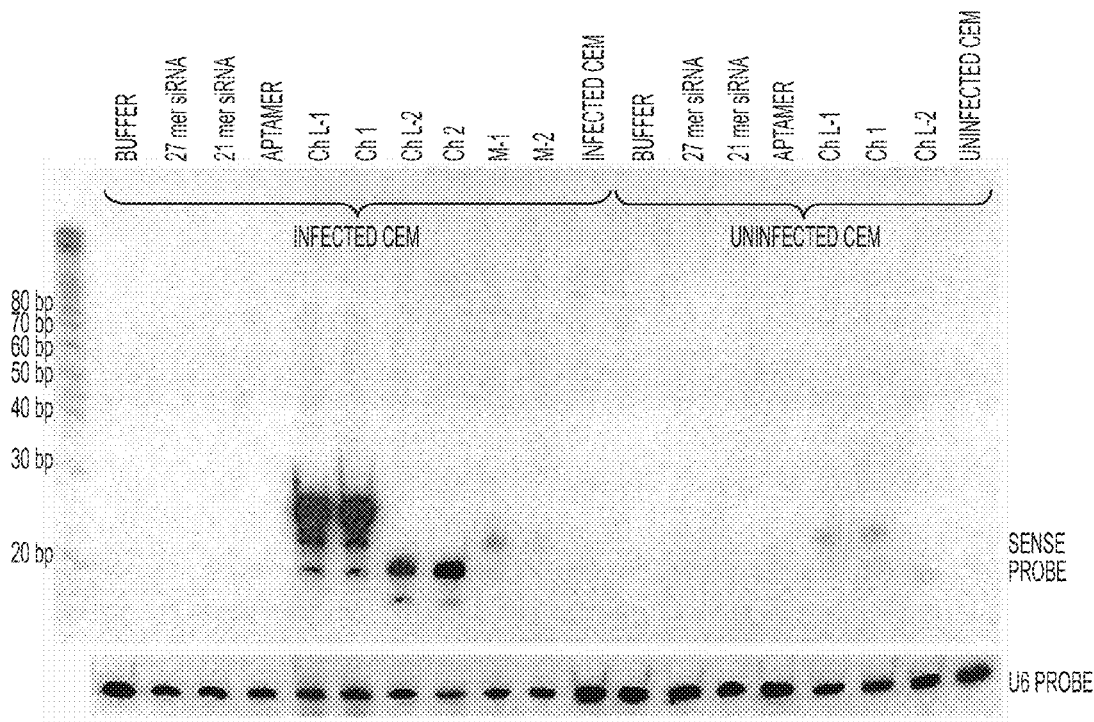
FIG. 5A show Northern blots of infected CEM cells. Infected CEM cells were directly treated with siRNA and Chimeras. The 27 Chimera RNA is partially processed to a 21 mer siRNA following uptake into the CEM cells. Total RNAs were hybridized with a 21-mer P$^{32}$-labeled oligonucleotide probe. U6 RNA was used as an internal loading control.

Anti-gp120 Aptamer-siRNA Chimeras Inhibit HIV gp120 Mediated Cell Fusion and HIV-1 Infection of CEM-T Cells Essential to the use of the aptamer-siRNA chimeras in treating HIV infection is that the aptamer allows internalization of the chimeras in HIV infected cells. We first demonstrated by Northern blot analyses that chimeric delivered siRNAs were detectable in HIV infected CEM cells directly which were treated with the chimeras. The Northern blotting data of FIG. 5A demonstrate that the siRNAs from chimera are internalized in HIV infected CEM cells since the 27 mer was processed to 21-23 base siRNAs in these cells, but not in the gp120-negative uninfected CEM cells, suggesting that the chimeras specifically delivered siRNA into the infected CEM cells through anti-gp120 aptamer. As expected, the 21 or 27 mer duplex siRNAs in absence of the aptamers were not detectable in the CEM cells owing to the lack of internalization (FIG. 5A). Since a little of non-specific bindings existed on the cells surface, tiny 21 or 27 mer RNA from chimeras (Ch L-1, Ch 1 and Ch L-2) also were hybridized in uninfected CEM.

Figure 5B:
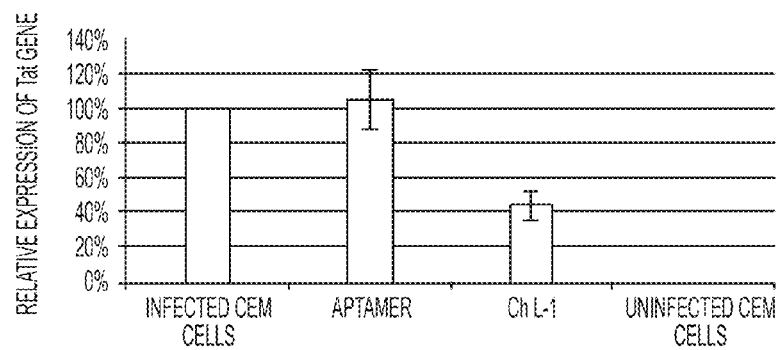
FIG. 5B shows aptamer-mediated inhibition of expression of tat/rev in infected CEM cells. Cells were incubated with the wild type aptamer or Ch L-1 for 7 days prior to RNA extraction. Gene expression for Tat/rev and GAPDH was assayed by qRT-PCR. Data represent the average of three replicates.

To further confirm siRNA function after internalization to infected CEM cells, qRT-PCR was preformed to evaluate the tat/rev gene expression. Aptamer or chimeras were added directly to media containing infected CEM cells. After 7 days, treated cells were harvested, the total RNA was extracted and the extent of tat/rev gene inhibition was determined by quantitative RT-PCR expression assays. We find that the treatment of infected CEM cells with the chimeras is able to induce silencing of the tat/rev gene, while the aptamer alone did not affect tat/rev gene expression (FIG. 5B). These results provide further support that the chimeric delivered siRNA triggers RNAi.

Figure 10A:
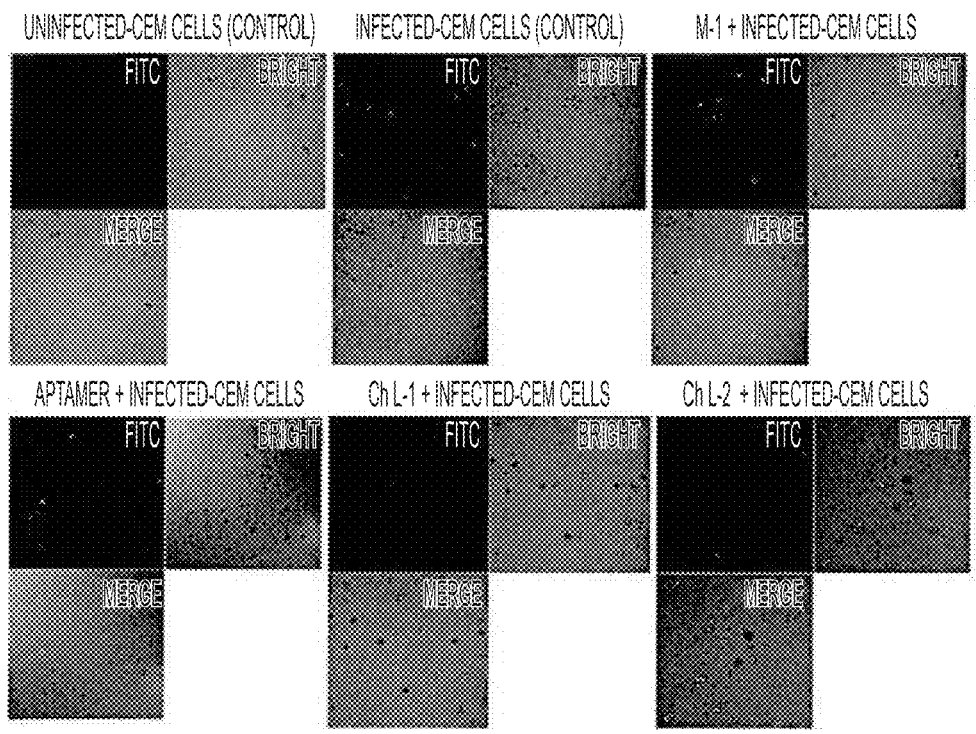
FIGS. 10A and 10B show an immunofluorescence assay of HIV-1 p17. HIV-1 infected CEM cells were incubated with 400 no aptamer or chimeras (Ch L-1 and Ch L-2) in culture medium for 24 hours (FIG. 10A) and 72 hours (FIG. 10B). Cells were washed with PBs, fixed, permeabilized and blocked with NGtS. After incubation with primary antibody (anti-p17), FITC-conjugated secondary antibody (Ho-α-Mu-FITC) was added to stain cells. Cells were washed, resuspended in 15 μL hard mounting medium and spotted on a microscopy slide for confocal microscopy.
Figure 10B:
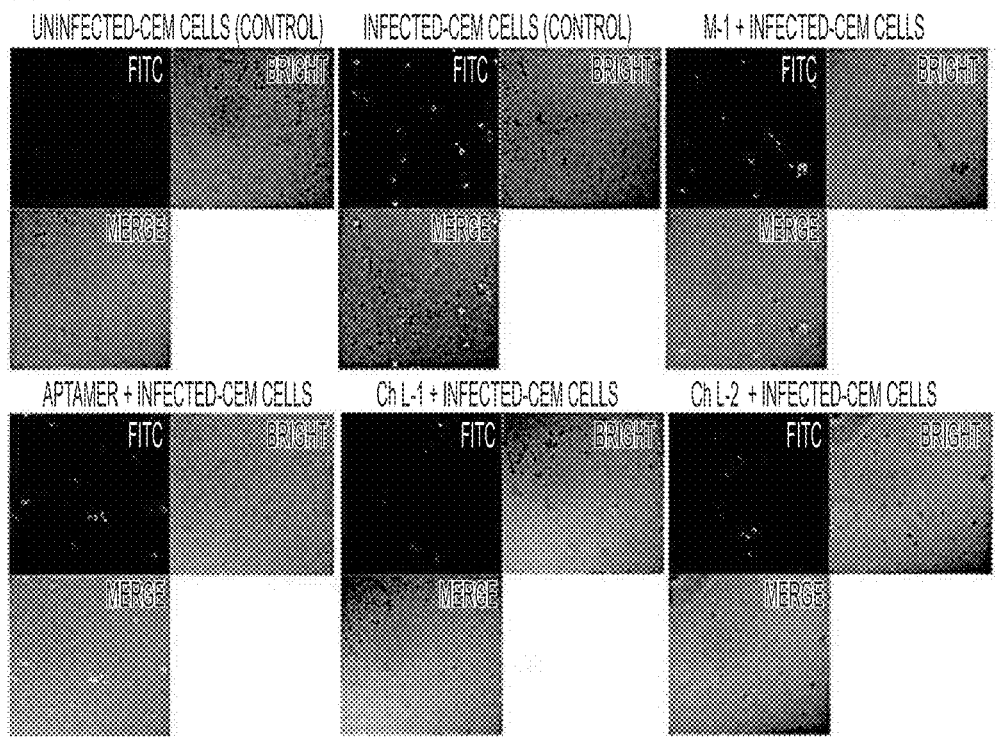

In HIV-1 infection, gp120 expressed at the cell surface will induce syncytia formation between infected and uninfected cells due to interactions between gp120 and CD4 (27, 28). We therefore sought to determine if the aptamer and chimeras would have an impact on syncitia formation in cell culture. In this assay, the HIV-1 infected-CEM cells were incubated with siRNA or chimeras RNAs. Subsequently, the uninfected MT2 cells expressing CD4 were added into infected-CEM cells treated with RNA. After 48 h of co-incubation at 37° C., cells syncytia were analyzed microscopically. The treatment of the HIV infected cultures with the aptamer and chimeras resulted in a clear reduction in syncytia formation (Data not presented). We also asked if the aptamer and chimeras prevent HIV replication in an acute infection assay by monitoring HIV-1 Gag p17 via an immunofluorescence assay (IF) (FIG. 10). These assays revealed a marked reduction in p17 expression in the HIV infected cells treated with the anti-gp120 aptamer and even more pronounced reduction with the Ch L1 chimera.

Figure 5C:
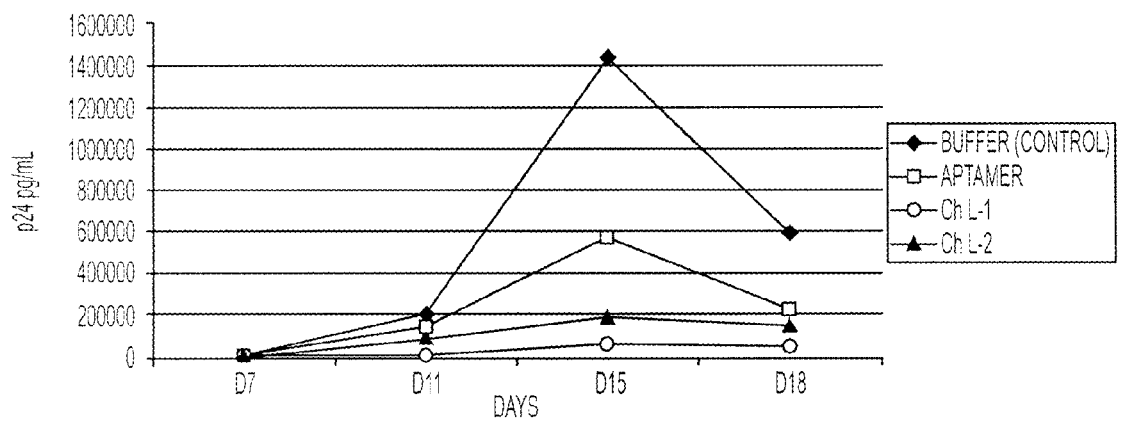
FIG. 5C shows that chimera RNAs inhibit HIV infection. HIV-1 NL4-3 was incubated with the various RNAs at 37° C. for 1 h. Subsequently, the treated virions were used to infect CEM cells. The culture supernatant was collected at different time (7 d, 11 d, 15 d and 18 d) for p24 antigen analyses. Data represent the average of duplicate assays.
Figure 5D:
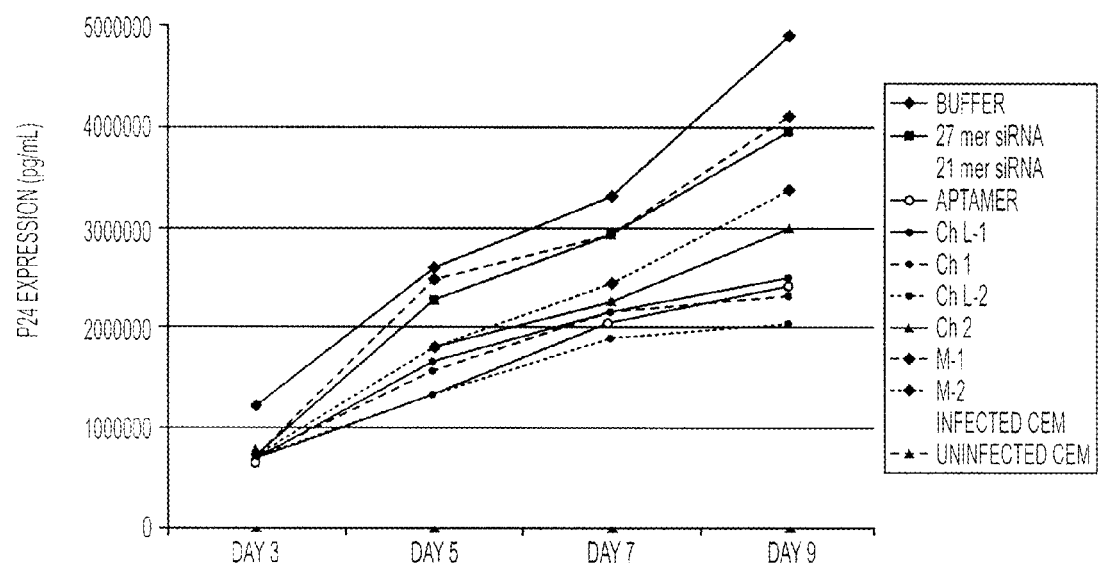
FIG. 5D shows that the siRNAs delivered by the chimera RNAs inhibit HIV-1 replication in previously infected CEM cells. 1.5×10$^4$ infected CEM cells and 3.5×10$^4$ uninfected CEM cells were incubated at 37 C with the various RNAs at a final concentration of 400 nM. The culture supernatant was collected at different time points (3 d, 5 d, 7 d and 9 d) for p24 antigen analyses. Data represent the average of triplicate measurements of p24.

To further verify the activity of the anti-HIV activity of the chimeras in inhibition of HIV-1 replication, we carried out the following assays. In the first assay, HIV-1 was first mixed with the chimeras or aptamer and subsequently the viruses were used to infect CEM cells. In this assay the infectivities of the aptamer or chimera treated virus were significantly reduced and viral replication was suppressed out to two weeks (FIG. 5C). Ch L-1 was the most effective inhibitory agent. In the second experiment, the aptamer or chimeras were incubated with HIV infected-CEM cells. At different days post treatment with the aptamer and chimeras, aliquots of the media were assayed for viral p24 antigen levels. The results of these analyses (FIG. 5D) showed that all of the aptamer containing RNAs inhibited p24 production, but the strongest inhibition was observed with Ch L-1 treatment, again consistent with our results from the other assays. These data, together with the inhibition of cell fusion and p17 expression, demonstrate that the anti-gp120 aptamer-siRNA chimera system can strongly inhibit HIV-1 replication and infection. Moreover, the suppression is attributed to the combined affect of the aptamer binding gp120 and RNAi.

Example 7

Anti-gp120 Aptamer-siRNA Chimeras do not Trigger an Interferon Response

Figure 6A:
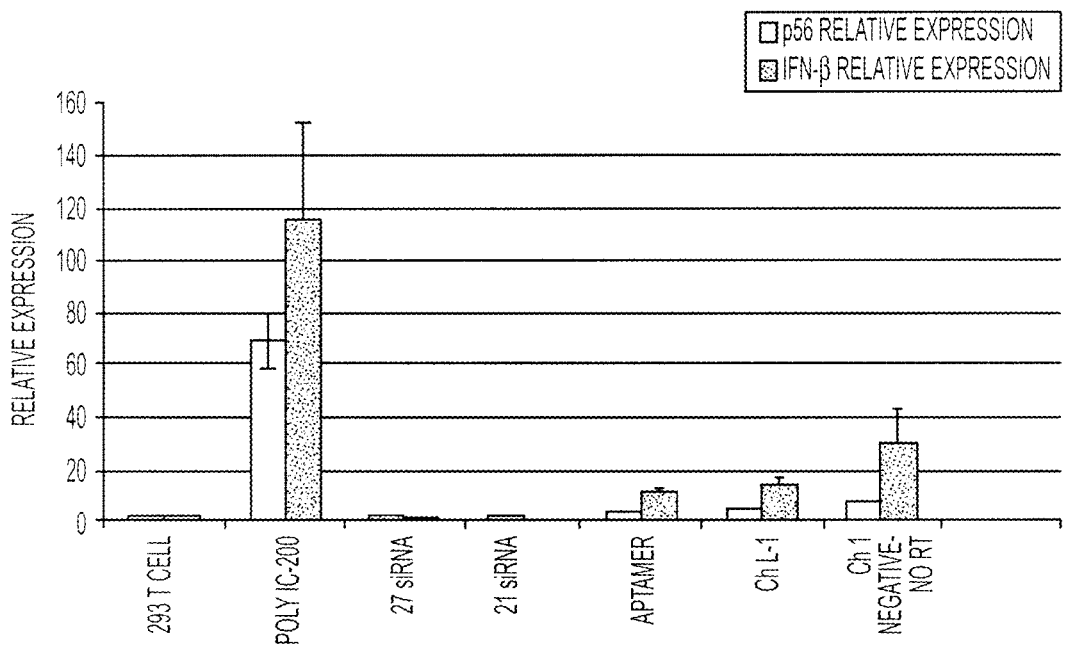
FIGS. 6A and 6B show IFN assays. IFN-β, the interferon response gene encoding P56 (CDKL2) and OAS1, mRNAs were measured by quantitative RT-PCR. The expression of these interferon response genes was, not significantly induced by the siRNAs or chimeric RNAs, whereas expression of these genes was induced by poly(IC) in HEK 293 cells (FIG. 6A) or by IFN-alpha in infected CEM cells (FIG. 6B). Gene expression levels are normalized to GAPDH mRNA expression levels. The data represent the average of triplicate measurements.
Figure 6B:
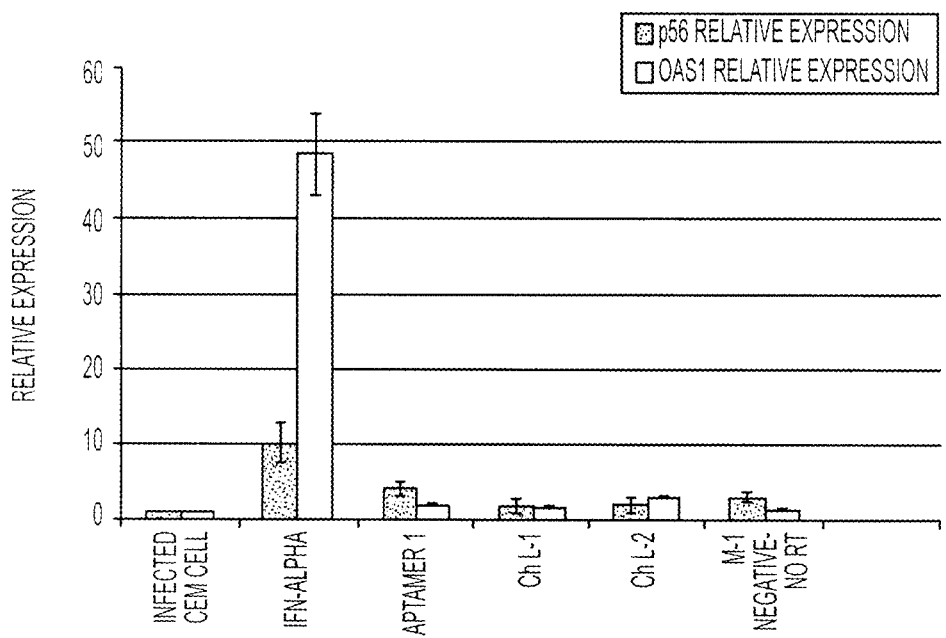

It has been reported previously that siRNAs delivered by liposomes or polyplex reagents can non-specifically activate inflammatory cytokine production (TNFα, IL-6 and IL-12) as well as IFN responsive genes, which in turn can trigger cellular toxicity (38-40). We therefore assessed the induction of type I interferon regulated gene expression by our anti-gp120 aptamer-siRNA chimeras using quantitative RT-PCR expression assays. As a positive control, we incubated the target cells with poly(IC). We find that the treatment of HEK293 cells with the chimeras did not significantly induce expression of the interferon-β and p56 genes (FIG. 6A). Since CEM cells are difficult to be transfected with control molecules such as poly (IC), we used IFN-α as a positive control to confirm upregulation of p56 and OAS1 gene expression. As we observed in the HEK293 transfection assays, treatment of CEM cells with the chimeras did not induce type I IFN responses (FIG. 6B). Similar results were obtained using HIV infected CEM cells treated with the chimeras, suggesting that the gp120 mediated internalization of the chimeras does not trigger toxic IFN responses.

Example 8

Discussion of Examples 1-7

Aptamers are nucleic acid species that have been engineered through repeated rounds of in vitro selection to bind to various molecular targets such as small organic molecules, proteins, nucleic acids, and even cells (41-43). Because aptamers are capable of binding with high specificity to their ligands at low nano- to picomolar dissociation constants they can be used as molecular drugs for both basic research and clinical purposes (44-48).

The success of RNAi-based clinical applications is dependent upon the efficiency of siRNA delivery to target cells. In this report, we have capitalized upon the exquisite specificity of a gp120 aptamer to deliver anti-HIV siRNAs into HIV infected cells with the net result that replication and spread of HIV is strongly inhibited by the combined action of the aptamer and siRNA targeting the tat/rev common exon of HIV-1.

We utilized the HIV-1 envelop protein gp120 as a model receptor for targeted intracellular delivery of anti-HIV siRNAs. Cell type-specific binding and uptake of chimeric aptamer-siRNA conjugates were achieved through the interaction of the aptamer portion with gp120 on the cell surface of infected cells. To insure the stability of our RNA chimeric molecules in sera, we utilized the RNA stabilizing 2'-Fluoro backbone modifications of pyrimidines on the aptamer and siRNA sense strand. The antisense strand was not chemically modified, but was in fact stabilized by virtue of its base pairing to the modified sense strand.

Notably, the cell type-specific gene silencing revealed that the siRNAs were successfully delivered into cells and entered into the RNAi pathway by interaction of the anti-gp120 aptamer with gp120 expressed on the cell surface. Interestingly, the chimeras containing a 27 mer duplex RNA gave better efficacy in gene silencing than the corresponding 21 mer duplex containing chimeras. The 27 mer duplex alone was also more potent than the 21 mer duplex when these RNAs were delivered by lipofection. We attribute this increased potency to Dicer processing of the 27 mer wherein the processed 21-23 mer siRNAs are more readily handed off to RISC. It is of interest that we never observed complete processing of the 27 mer into 21-23 mers in our Northern Blot analyses of cells treated with the chimeras. This may in part be a consequence of the high intracellular concentrations achieved by aptamer delivery, but may also reflect that the design of our blunt ended duplexes is sub-optimal for Dicer processing. We observed that rather than enter the duplex from the 2 base 3' overhang, Dicer cleavage initiated following entry onto the duplex from the blunt end of the duplex. To this end we are testing other structures of the siRNA portion of the aptamers to achieve more complete Dicing.

An interesting observation is that analyses of the target cleavage products by a 5'-RACE technique further demonstrated that neither the 27 mer nor 21 mer siRNAs underwent processing to trigger duplexes with two base 3' overhangs on both ends of the siRNAs. In fact for both the 21 mer and 27 mer derived siRNAs, the target mRNA was cleaved between positions 10 and 11 relative to the blunt 5' end of the siRNA antisense strand. These results suggest that unprocessed 27 mer as well as Dicer processed 27 mer antisense strands may be incorporated into RISC. Given the results from the cell extract Dicing reaction, which revealed that the 27 mer is not processed at the 5' end of the antisense but only at the 3' end, it is not possible to determine whether all, some or none of the activated RISC was derived from intact 27 mer antisense getting incorporated directly into RISC.

Aptamers that bind to viral or cellular proteins with high affinity and specificity are useful for therapeutic applications. In this study, both aptamer and chimeras can dramatically suppress the replication and production of HIV-1 in a variety of assays. These results demonstrate important attributes of the anti-gp120 aptamer as both inhibitors of HIV via direct binding to virion or intracellular gp120 and as a cell type specific delivery vector for therapeutic siRNAs.

Because the anti-gp120 aptamer is responsible for the targeted delivery of siRNAs, gp120 expression is necessary for cell type-specific transport. This is in essence a safety feature which could be capitalized upon to deliver siRNAs that target HIV or even cellular messages essential for viral replication. Since only HIV infected cells would bear the inhibitory action of the siRNA, this approach greatly minimizes potential off-target effects by the siRNAs.

The dual inhibitory potential of the aptamer-siRNA fusion is an important point of discussion. Both the aptamer and chimeras showed strong inhibition of syncitial cell formation, expression of HIV-1 Gag p17 and HIV replication and spreading in HIV-1 infected-CEM T-lymphocytes. The anti-gp120 aptamer neutralizes HIV-1 infectivity via blocking the interaction of gp120 and CD4, and the siRNA silences tat/rev expression. Thus, the anti-gp120/HIV chimeras serve a double-function and therefore provide greater efficacy than either the aptamer or siRNA applied alone. Finally, we show that the aptamer mediated delivery of siRNAs via binding to gp120 and subsequent internalization does not trigger type I interferon gene responses in different cell lines.

In summary, this strategy provides a new paradigm for delivery of anti-HIV siRNAs by allowing selective delivery to HIV infected cells and dual function inhibition of HIV replication and spread. Moreover, the aptamer and siRNAs can be readily changed to accommodate genetic changes in the virus, making, making this an attractive approach for systemic anti-HIV therapy.

Example 9

Materials and Methods for Example 10

Generation of aptamer and chimera RNAs by in vitro transcription: Aptamer and chimeras RNA were prepared as described above. Specially, the sense strands of aptamer-siRNA chimeras were underlined. The italic UU was the linker between the aptamer portion and siRNA portion. A-1 aptamer: 5'-GGGAGGACGAUGCGGAAUUGAGGGAC-CACGCGCUG CUUGUUGUGAUAAGCAGUUU-GUCGUGAUGGCAGACGACUCGCCCGA-3' (SEQ ID NO:8); B-68 aptamer: 5'-GGGAGGACGAUGCGGA-CAUAGUAAUGACACGGAGGAUGG AGAAAAAA-CAGCCAUCUCUUGACGGUCAGACGACUCGCCCGA-3' (SEQ ID NO:9); Chimera A-1-sense strand: 5'-GGGAGGACGAUGCGGAAUUGAGGGACCACGC GCUGCUUGUUGUGAUAAGCAGUUU-GUCGUGAUGGCAGACGACUCGCCCGAUU GCGGAGACAGCGACGAAGAGCUCAUCA-3' (SEQ ID NO:32); Chimera B-68-sense strand: 5'-GGGAGGAC-GAUGCGGACAUAGUAAUGACACGGAG-GAUGGAGAAAAAACAGCC AUCUCUUGACGGUCA-GACGACUCGCCCGAUU GCGGAGACAGCGACGAAGAGCUCAUCA-3' (SEQ ID NO:33); Antisense strand: 5'-UGAUGAGCUCU-UCGUCGCUGUCUCCG CdTdT-3' (SEQ ID NO:2).

Gel shift assays and determination of dissociation constant: The RNA aptamers were treated by calf intestine phosphatase (CIP) to remove the initiating 5'-triphosphate and were subsequently labeled at the 5' termini with T4 polynucleotide kinase and $\gamma$-$^{32}$P-ATP. The gp120 protein was serially diluted to the desired concentrations (0-640 nM). A constant amount of end-labeled RNA (10 nM) was incubated with corresponding concentrations gp120 protein in binding buffer (10 mM HEPES pH 7.4, 150 mM NaCl, 1 mM $CaCl_2$, 1 mM $MgCl_2$, 2.7 mM KCl, 10 mM DTT, 0.01% BSA and tRNA) at room temperature. After 30 min of incubation, 20 µL of binding reaction was loaded onto a 5% non-denaturing polyacrylamide gel. The gel was exposed to a Phosphor imaging screen and quantified using a Typhoon scanner. The dissociation constants were calculated using non-linear curve regression with a Graph Pad Prism.

Cell culture: HEK 293 cells and CEM cells were purchased from ATCC and cultured in DMEM and RPMI 1640 supplemented with 10% FBS respectively, according to their respective data sheets. CHO-WT and CHO-EE cells were obtained through the AIDS Research and Reference Reagent Program, Division of AIDS, NIAID, NIH. They are grown in GMEM-S. Cells were cultured in a humidified 5% $CO_2$ incubator at 37° C. PBMC. Blood samples were obtained from healthy donors from the City of hope National Medical Center (clinic personnel). PBMC were isolated from whole blood by centrifugation through Ficoll-Hypaque solution (Histopaque-1077, Sigma). CD8 cells (T-cytotoxic/suppressor cells) were depleted from PBMC by using Dynabeads CD8 (Invitrogen, CA) according to the manufacturer's instructions. CD8+ T cell-depleted PBMC were washed twice in PBS and resuspended in culture medium (RPMI 1640 with 10% FBS, 1× PenStrep and 100 U/mL interleukin-2). Cells were cultured in a humidified 5% $CO_2$ incubator at 37° C.

Cell-surface binding of aptamer-siRNA chimeras (low cytometry analysis): CHO-WT gp160 or CHO-EE cells were washed with PBS, trypsinized and detached from the plates. After washing cells twice with 500 µL binding buffer. Cell pellets were resuspended in binding buffer and incubated at 37° C. for 30 min. Cells were then pelleted and resuspended in 50 µL of prewarmed binding buffer containing either 400 nM Cy3-labeled aptamer or Chimera RNAs. After incubation at 37° C. for 40 min, cells were washed three times with 500 µL of prewarmed binding buffer, and finally resuspended in 350 µL of binding buffer prewarmed to 37° C. and analyzed by flow cytometry.

Cellular binding and uptake studies (confocal microscopy analysis): The CHO-gp160 and CHO-EE cells lines were grown in an 8-well chambered-slide with seeding at 0.5×10$^5$ in GMEM-S medium to allow about 70% confluence in 24 h. On the day of the experiments, cells were washed with 250 µL of prewarmed PBS and incubated with 250 µL of prewarmed complete growth medium for 30 min at 37° C. Cy3-labeled RNAs at 40 nM final concentration were added into the media and incubated at 37° C. for 2 hrs. Subsequently, cells were washed three times with 250 µL of prewarmed PBS, fixed with 4% formaldehydes for 15 min. The cells were stained by treatment with 100 µL of Vybrant Cell-Labeling Solution (DIO membrane dye, Molecular Probes, Invitrogen) according to the manufacturer's instructions. The images were collected using a Zeiss LSM 510 upright 2 photon confocal microscopy system under water immersion at 40 magnifications.

HIV-1 challenges and p24 antigen assay: CEM cells or PBMCs were infected with HIV IIIB or NL4-3 for 5 days. Prior to aptamer treatments the infected cells were gently washed with PBS three times to remove free virus. 2×10$^4$ infected cells and 3×10$^4$ uninfected cells were incubated with refolded RNAs at 400 nM final concentration in 96-well plates at 37° C. The culture supernatants were collected at different times (3 d, 5 d, 7 d, 9 d and 11 d). The p24 antigen analyses were performed using a Coulter HIV-1 p24 Antigen Assay (Beckman Coulter) according to the manufacturer's instructions.

qRT-PCR analysis: CEM cells were infected with HIV IIIB or NL4-3 for 5 days. Prior to analyses, the infected-CEM cells were gently washed 3 times to eliminate free virus. The infected CEM cells were treated directly with the aptamer or Ch L-1 (400 nM). After 7 days, total RNAs were isolated with STAT-60 (TEL-TEST "B", Friendswood, Tex.). Expression of the tat/rev coding RNAs was analyzed by quantitative RT-PCR using 2x iQ SyberGreen Mastermix (BIO-RAD) and specific primer sets at a final concentration of 400 nM. Primers were as follows: tat/rev forward primer: 5'-GGCGT-TACTCGACAGAGGAG-3' (SEQ ID NO:22); tat/rev reverse primer: 5'-TGCTTTGATAGAGAAGCTTGATG-3' (SEQ ID NO:23); GAPDH forward primer 1: 5'-CATTGACCT-CAACTACATG-3' (SEQ ID NO:24); GAPDH reverse primer 2: 5'-TCTCCATGGTGGTGAAGAC-3' (SEQ ID NO:25). RNA-Stat60 was used to extract total RNA according to the manufacturer's instruction (Tel-Test). Residual DNA was digested using the DNA-free kit per the manufacturer's instructions (Ambion). cDNA was produced using 2 μg of total RNA Moloney murine leukemia virus reverse transcriptase and random primers in a 15 μL reaction according to the manufacturer's instructions (Invitrogen). GAPDH expression was used for normalization of the qPCR data.

Example 10

2'-F-Substituted Aptamers

Figure 11A:
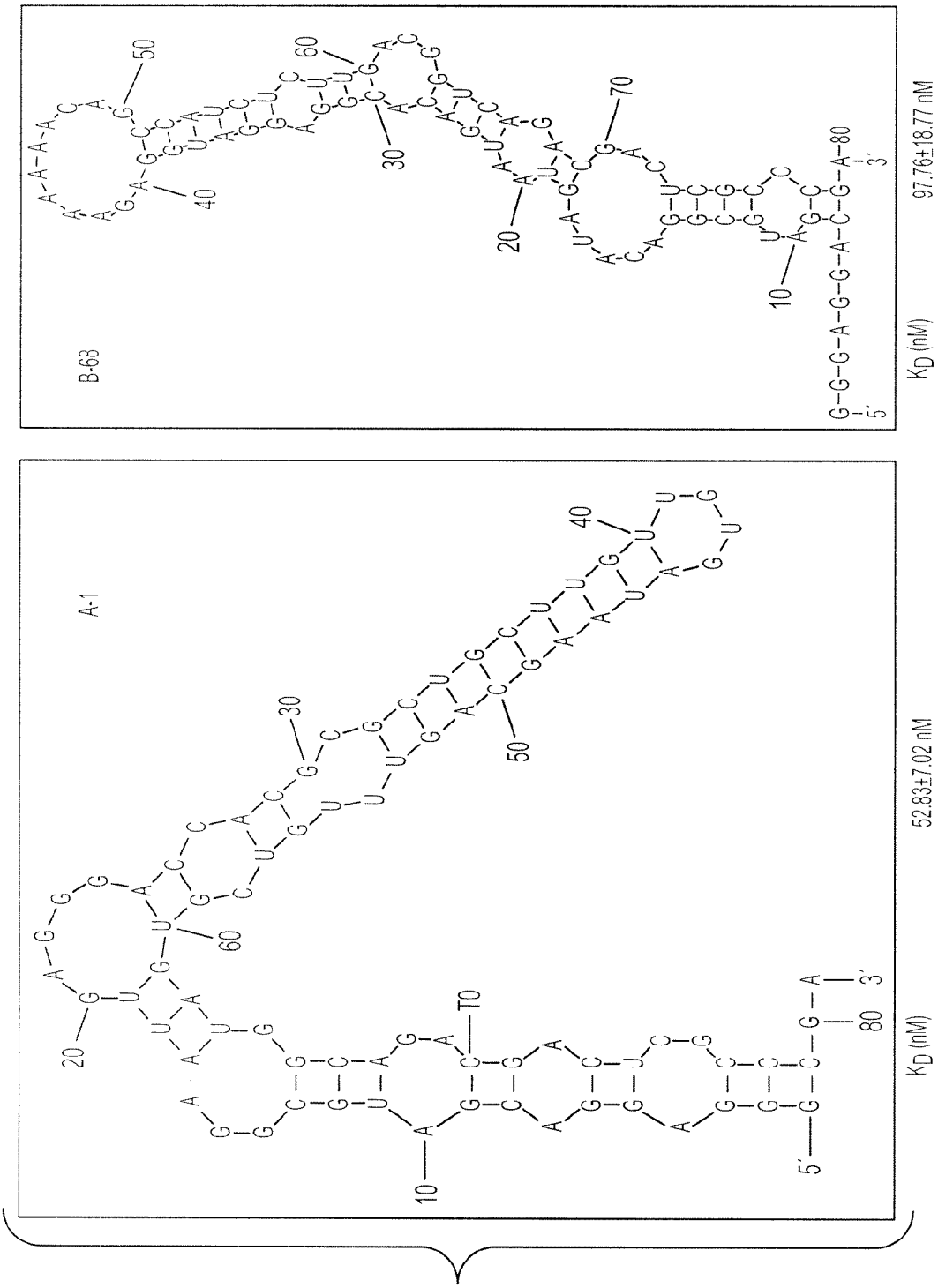
FIGS. 11A-11C show the secondary structure and binding activity assay of selected aptamers against HIV-1$_{Bal}$ gp120.
Figure 11B:
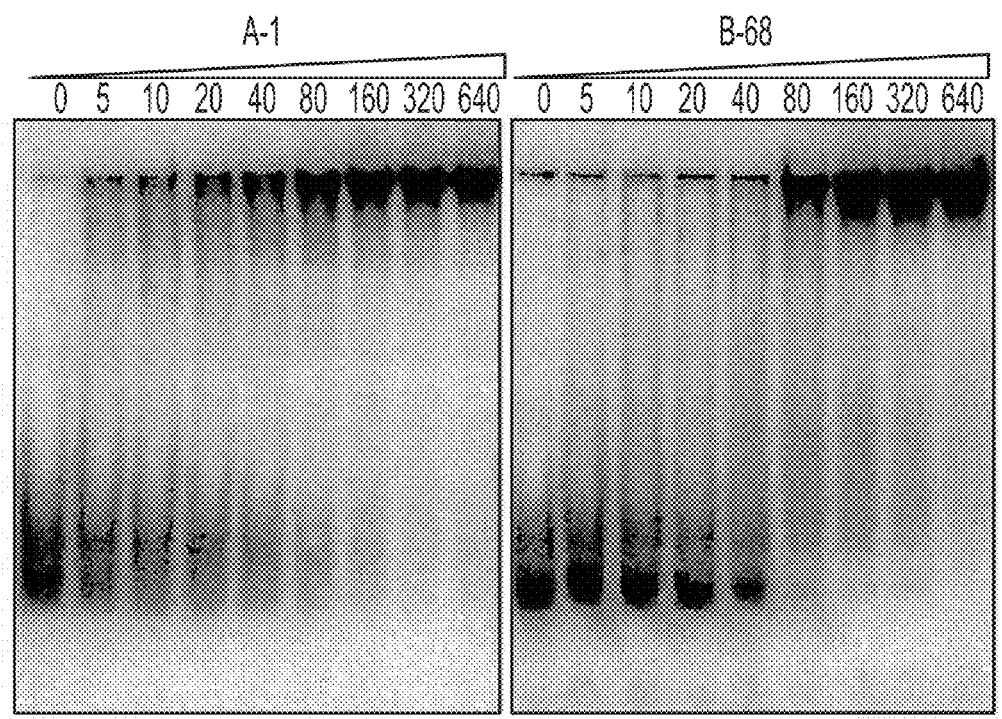
Figure 11C:
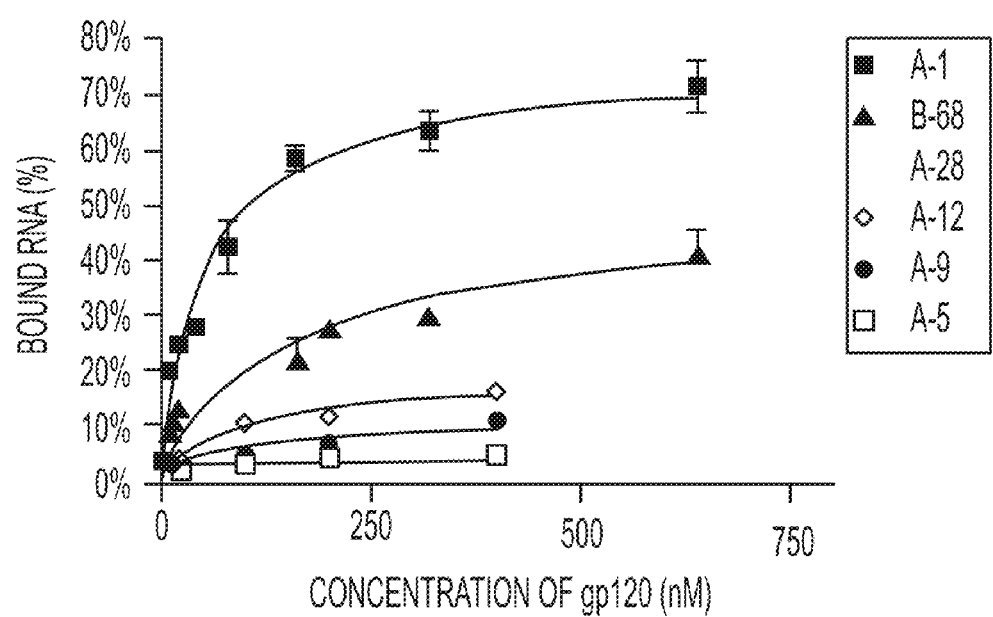
Figure 12A:
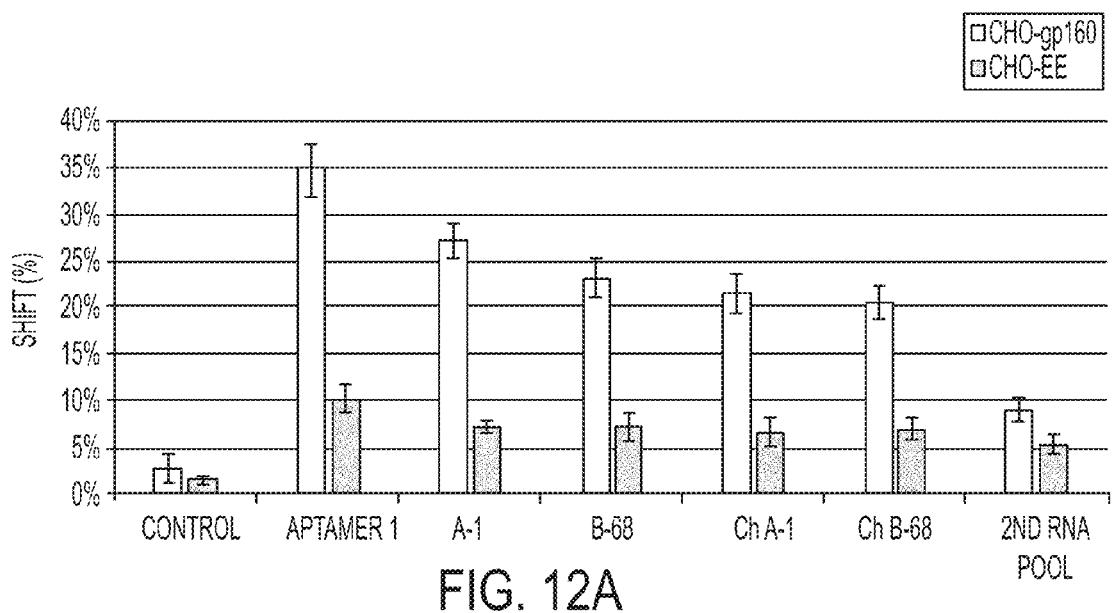
FIGS. 12A and 12B show binding and uptake of aptamer A-1 to CHO-gp160 cells.
Figure 12B:
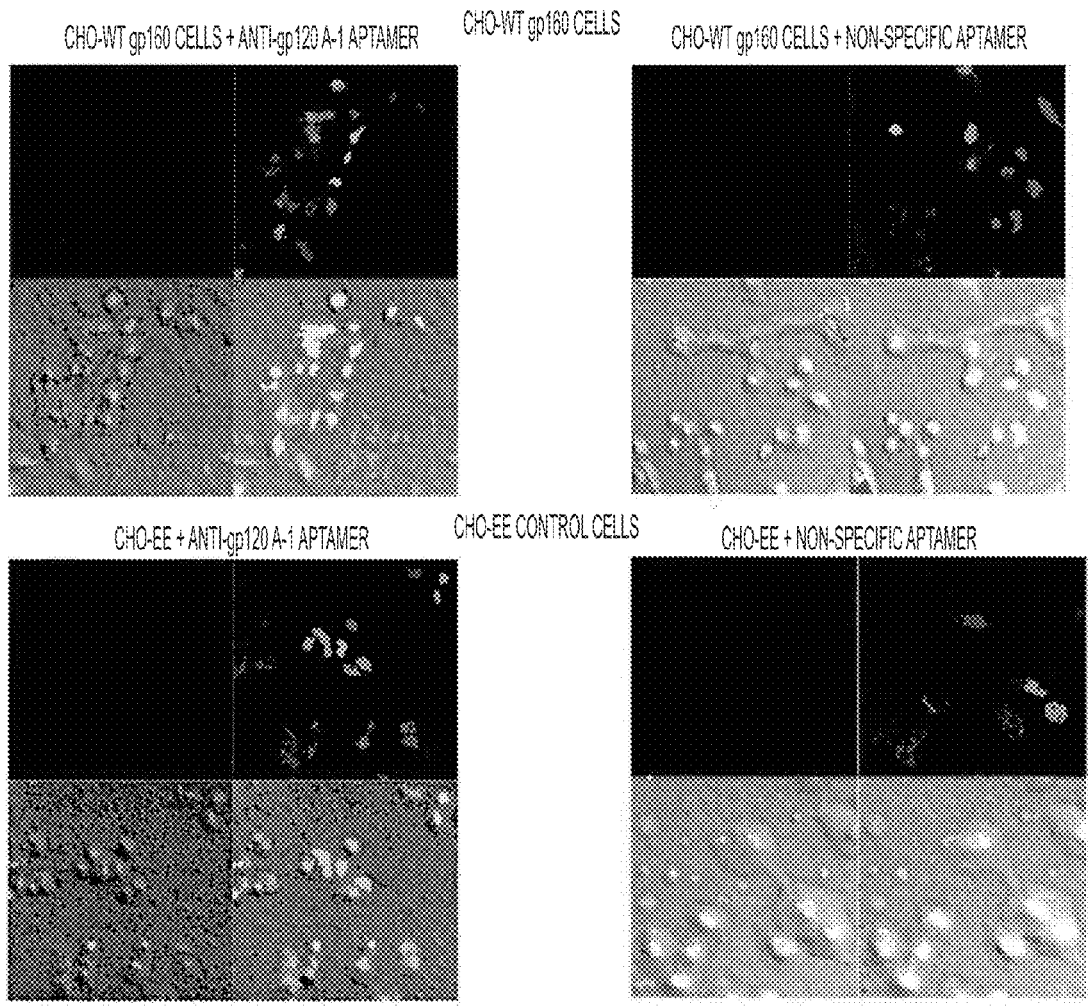
Figure 13:
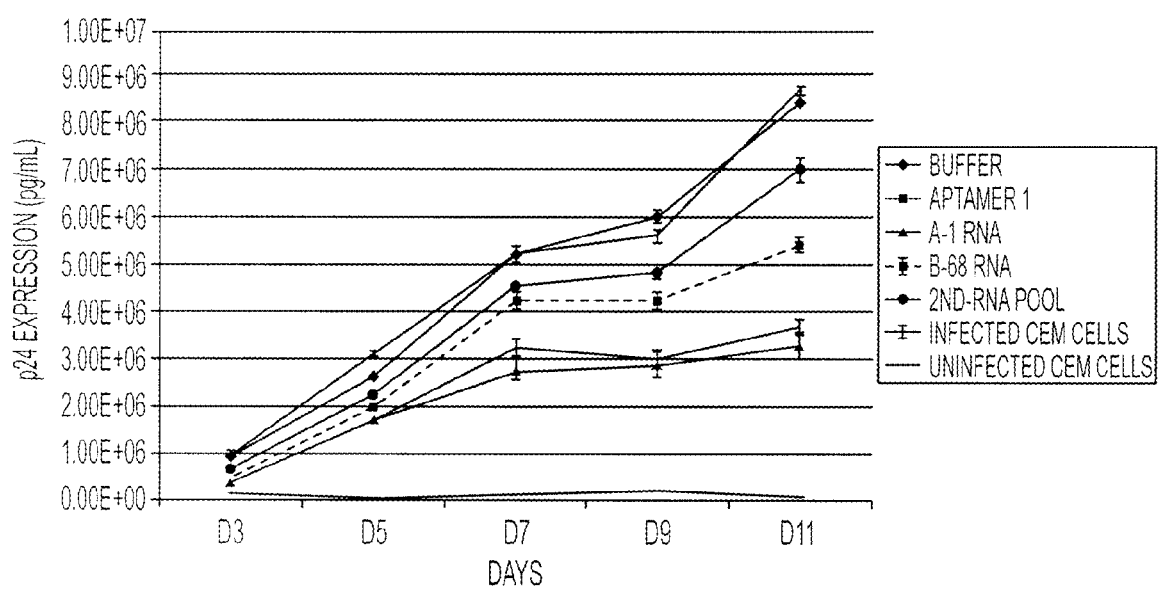
FIG. 13 shows that the selected anti-gp120 aptamers inhibited HIV-1 replication in previously infected CEM cells. 1.5× 10$^4$ infected CEM cells and 3.5×104 uninfected CEM cells were incubated at 37° C. with the various RNAs at a final concentration of 400 nM. The culture supernatant was collected at different time points (3 d, 5 d, 7 d, 9 d and 11 d) for p24 antigen analyses. Data represent the average of triplicate measurements of p24.
Figure 14A:
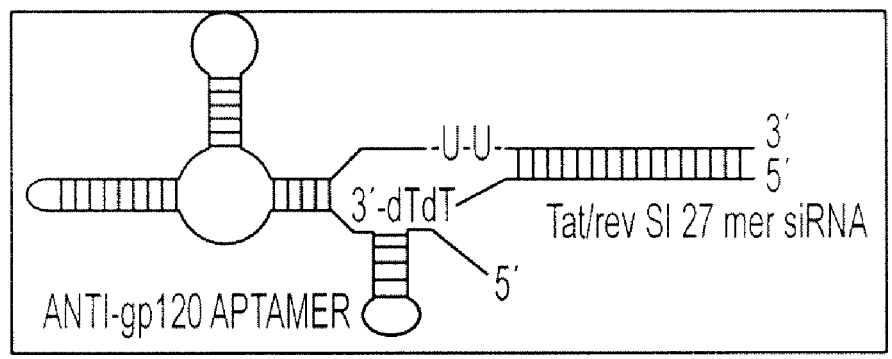
FIGS. 14A and 14B show the aptamer-based approach for siRNA delivery.
Figure 14B:
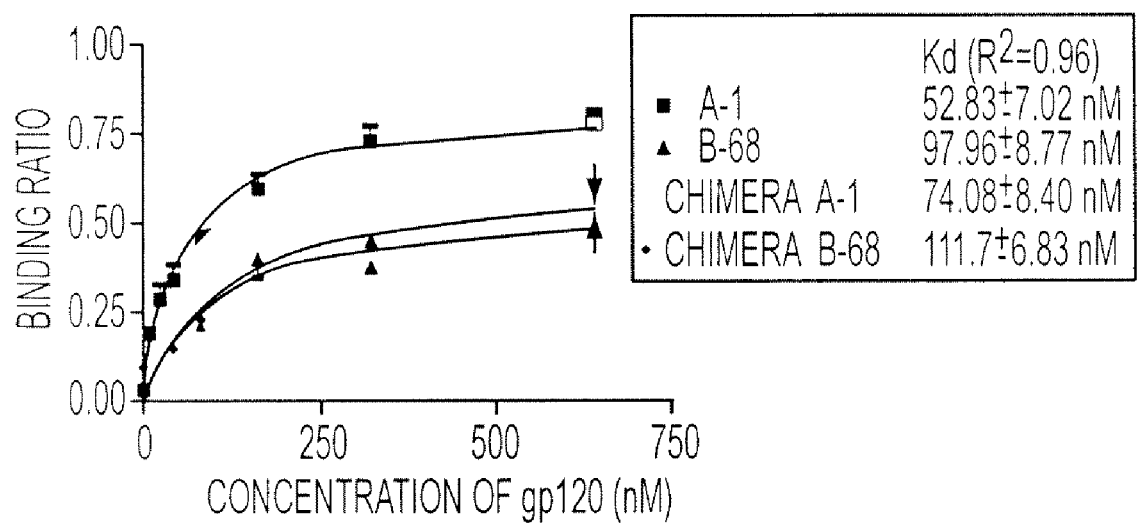
Figure 15A:
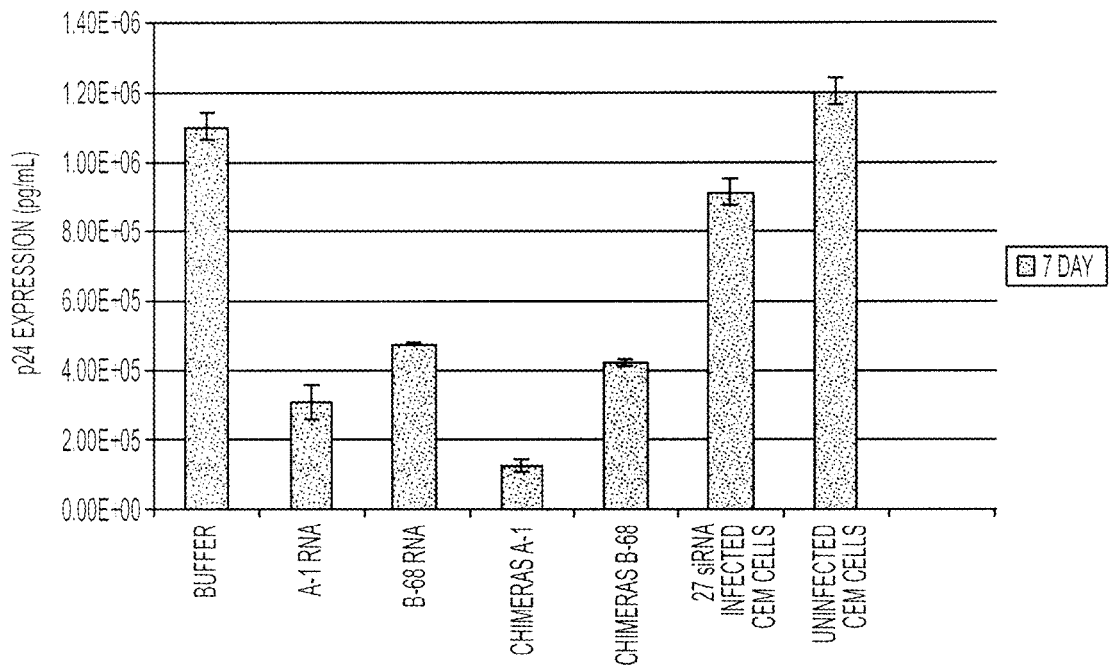
FIGS. 15A-15D show dual inhibition on HIV-1 infection mediated by aptamer-siRNA chimeras. Both anti-gp120 aptamer and aptamer-siRNA chimeras neutralized the HIV-1 infection in CEM cells (FIG. 15A) and PBMC culture (FIG. 15C), respectively. The chimeras (Ch A-1/Ch B-68) showed better inhibition than aptamer alone. The siRNA delivered by aptamers down-regulated target gene expression in CEM (FIG. 15B) and PBMC (FIG. 15D) as measured by Tat/Rev expression (qRT-PCR).
Figure 15B:
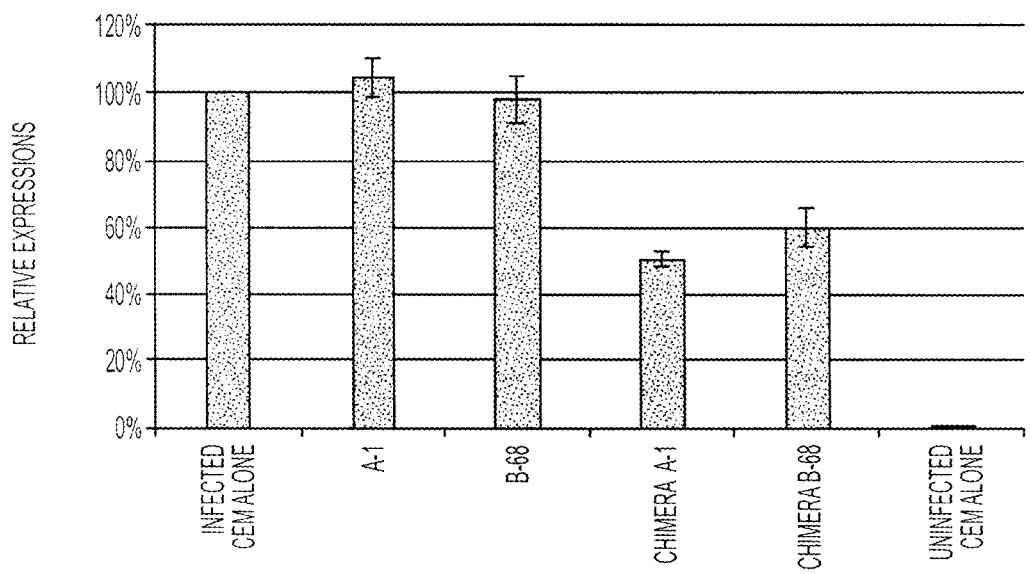
Figure 15C:
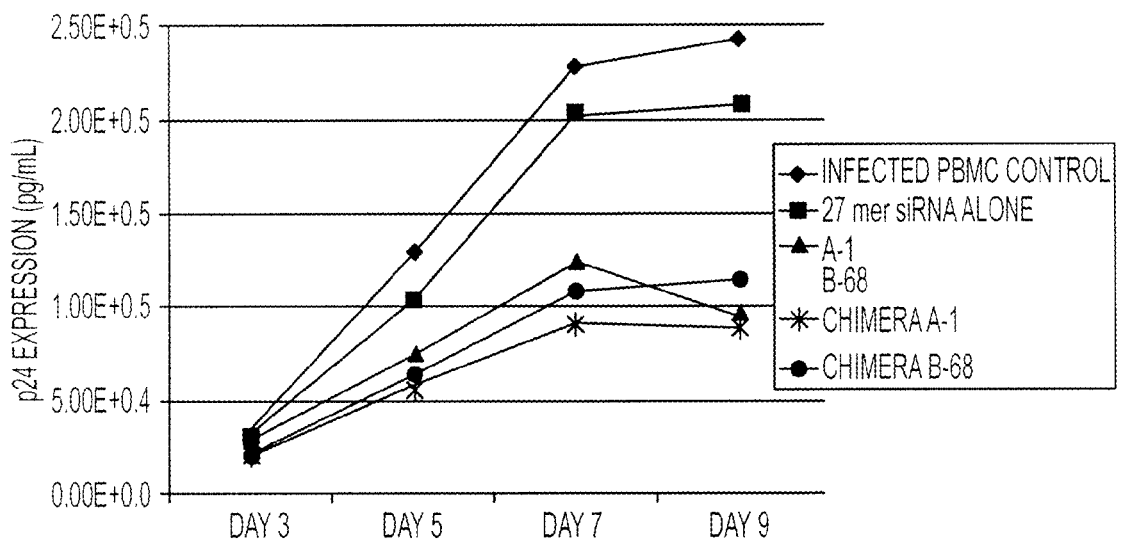
Figure 15D:
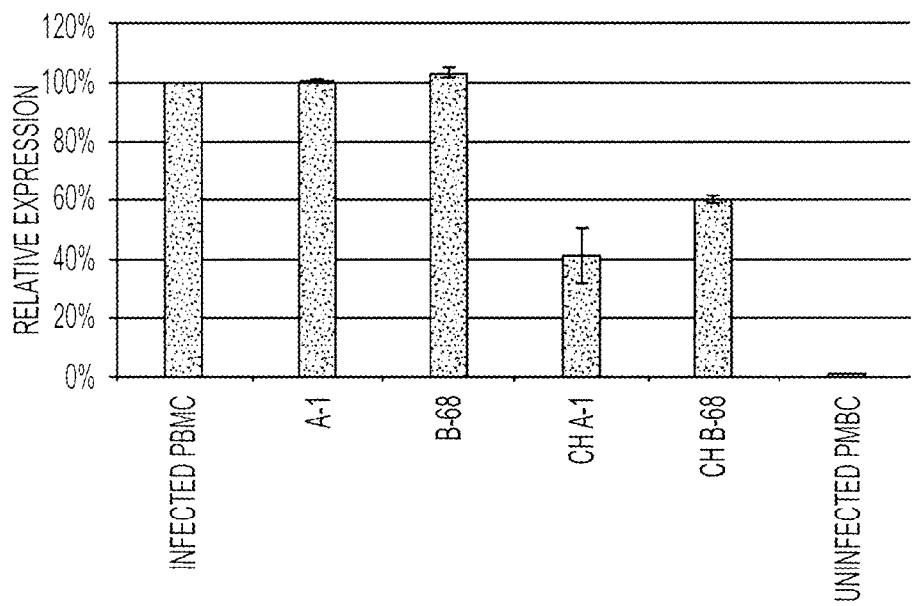

We described above a novel dual inhibitory function anti-gp120 aptamer-siRNA chimera delivery system for HIV-1 therapy. In order to increase the applicability and efficacy of aptamers in clinical therapy, in the present of study, new 2'-F substituted RNA aptamers that bind to the HIV-1$_{Ba-L}$ gp120 protein were isolated from an RNA library by using a process called SELEX (Systematic Evolution of Ligands by EXponential enrichment) (41, 42, 44, 45). Scintillation measurement and gel shift assays showed that the selected RNA aptamers (FIG. 11A) specifically bind to the target protein with low to mid nanomolar dissociation constants (FIG. 11B). Flow cytometry data (FIG. 12A) and confocal microscopy (FIG. 12B) indicated that the aptamers are able to specifically bind and be internalized by cells expressing HIV gp160. In addition, these aptamers also have been shown to potently neutralize a broad range of HIV-1 strains (FIG. 13). Further, we have developed aptamer-siRNA chimeric RNAs (FIGS. 14A and 14B) to specifically deliver functional siRNAs into HIV-1 infected cells. These chimeras RNA also specifically inhibit HIV-1 infectivity in human leukemic CEM cells (FIGS. 15A and 15B) and Peripheral Blood Mononuclear cells (PBMC) culture (FIGS. 15C and 15D).

These results demonstrate that the aptamers are not only expected to provide an inhibitor to fight HIV-1, but also act as delivery molecules for siRNAs and perhaps other small RNA inhibitors.

BIBLIOGRAPHY

1. Fire, A. et al. Potent and specific genetic interference by double-stranded RNA in *Caenorhabditis elegans. Nature* 391, 806-11 (1998).
2. Kim, D. H. & Rossi, J. J. Strategies for silencing human disease using RNA interference. *Nat Rev Genet.* 8, 173-84 (2007).
3. Behlke, M. A. Progress towards in vivo use of siRNAs. *Mol Ther* 13, 644-70 (2006).
4. Layzer, J. M. et al. In vivo activity of nuclease-resistant siRNAs. *RNA* 10, 766-71 (2004).
5. Morrissey, D. V. et al. Activity of stabilized short interfering RNA in a mouse model of hepatitis B virus replication. *Hepatology* 41, 1349-56 (2005).
6. Lewis, D. L. & Wolff, J. A. Delivery of siRNA and siRNA expression constructs to adult mammals by hydrodynamic intravascular injection. *Methods Enzymol* 392, 336-50 (2005).
7. Kishida, T. et al. Sequence-specific gene silencing in murine muscle induced by electroporation-mediated transfer of short interfering RNA. *J Gene Med* 6, 105-10 (2004).
8. Akaneya, Y., Jiang, B. & Tsumoto, T. RNAi-induced gene silencing by local electroporation in targeting brain region. *J Neurophysiol* 93, 594-602 (2005).
9. Inoue, A. et al. Electro-transfer of small interfering RNA ameliorated arthritis in rats. *Biochem Biophys Res Commun* 336, 903-8 (2005).
10. Tsunoda, S. et al. Sonoporation using microbubble BR14 promotes pDNA/siRNA transduction to murine heart. *Biochem Biophys Res Commun* 336, 118-27 (2005).
11. Kim, T. W. et al. Modification of professional antigen-presenting cells with small interfering RNA in vivo to enhance cancer vaccine potency. *Cancer Res* 65, 309-16 (2005).
12. Soutschek, J. et al. Therapeutic silencing of an endogenous gene by systemic administration of modified siRNAs. *Nature* 432, 173-8 (2004).
13. Hassani, Z. et al. Lipid-mediated siRNA delivery down-regulates exogenous gene expression in the mouse brain at picomolar levels. *J Gene Med* 7, 198-207 (2005).
14. Spagnou, S., Miller, A. D. & Keller, M. Lipidic carriers of siRNA: differences in the formulation, cellular uptake, and delivery with plasmid DNA. *Biochemistry* 43, 13348-56 (2004).
15. Wang, S. et al. Delivery of antisense oligodeoxyribonucleotides against the human epidermal growth factor receptor into cultured KB cells with liposomes conjugated to folate via polyethylene glycol. *Proc Natl Acad Sci USA* 92, 3318-22 (1995).
16. Wagner, E. et al. Transferrin-polycation conjugates as carriers for DNA uptake into cells. *Proc Natl Acad Sci USA* 87, 3410-4 (1990).
17. Schiffelers, R. M. et al. Cancer siRNA therapy by tumor selective delivery with ligand-targeted sterically stabilized nanoparticle. *Nucleic Acids Res* 32, e149 (2004).
18. Pun, S. H. et al. Cyclodextrin-modified polyethylenimine polymers for gene delivery. *Bioconjug Chem* 15, 831-40 (2004).
19. Hu-Lieskovan, S. et al. Sequence-specific knockdown of EWS-FLI1 by targeted, nonviral delivery of small interfering RNA inhibits tumor growth in a murine model of metastatic Ewing's sarcoma. *Cancer Res* 65, 8984-92 (2005).
20. Weissleder, R. et al. Cell-specific targeting of nanoparticles by multivalent attachment of small molecules. *Nat Biotechnol* 23, 1418-23 (2005).
21. Sorgi, F. L., Bhattacharya, S. & Huang, L. Protamine sulfate enhances lipid-mediated gene transfer. *Gene Ther* 4, 961-8 (1997).
22. Simeoni, F., Morris, M. C., Heitz, F. & Divita, G. Insight into the mechanism of the peptide-based gene delivery system MPG: implications for delivery of siRNA into mammalian cells. *Nucleic Acids Res* 31, 2717-24 (2003).
23. Muratovska, A. & Eccles, M. R. Conjugate for efficient delivery of short interfering RNA (siRNA) into mammalian cells. *FEBS Lett* 558, 63-8 (2004).
24. Simeoni, F., Morris, M. C., Heitz, F. & Divita, G. Peptide-based strategy for siRNA delivery into mammalian cells. *Methods Mol Biol* 309, 251-60 (2005).
25. McNamara, J. O., 2nd et al. Cell type-specific delivery of siRNAs with aptamer-siRNA chimeras. *Nat Biotechnol* 24, 1005-15 (2006).

26. Chu, T. C., Twu, K. Y., Ellington, A. D. & Levy, M. Aptamer mediated siRNA delivery. *Nucleic Acids Res* 34, e73 (2006).
27. Kwong, P. D. et al. Structure of an HIV gp120 envelope glycoprotein in complex with the CD4 receptor and a neutralizing human antibody. *Nature* 393, 648-59 (1998).
28. Kwong, P. D. et al. Structures of HIV-1 gp120 envelope glycoproteins from laboratory-adapted and primary isolates. *Structure* 8, 1329-39 (2000).
29. Kim, D. H. et al. Synthetic dsRNA Dicer substrates enhance RNAi potency and efficacy. *Nat Biotechnol* 23, 222-6 (2005).
30. Rose, S. D. et al. Functional polarity is introduced by Dicer processing of short substrate RNAs. *Nucleic Acids Res* 33, 4140-56 (2005).
31. Khati, M. et al. Neutralization of infectivity of diverse R5 clinical isolates of human immunodeficiency virus type 1 by gp120-binding 2'F-RNA aptamers. *J Virol* 77, 12692-8 (2003).
32. Dey, A. K. et al. An aptamer that neutralizes R5 strains of human immunodeficiency virus type 1 blocks gp120-CCR5 interaction. *J Virol* 79, 13806-10 (2005).
33. Dey, A. K., Griffiths, C., Lea, S. M. & James, W. Structural characterization of an anti-gp120 RNA aptamer that neutralizes R5 strains of HIV-1. *Rna* 11, 873-84 (2005).
34. Czauderna, F. et al. Structural variations and stabilising modifications of synthetic siRNAs in mammalian cells. *Nucleic Acids Res* 31, 2705-16 (2003).
35. Braasch, D. A. et al. RNA interference in mammalian cells by chemically-modified RNA. *Biochemistry* 42, 7967-75 (2003).
36. Morrissey, D. V. et al. Potent and persistent in vivo anti-HBV activity of chemically modified siRNAs. *Nat Biotechnol* 23, 1002-7 (2005).
37. Allerson, C. R. et al. Fully 2'-modified oligonucleotide duplexes with improved in vitro potency and stability compared to unmodified small interfering RNA. *J Med Chem* 48, 901-4 (2005).
38. Kim, D. H. et al. Interferon induction by siRNAs and ssRNAs synthesized by phage polymerase. *Nat Biotechnol* 22, 321-5 (2004).
39. Schlee, M., Hornung, V. & Hartmann, G. siRNA and is RNA: two edges of one sword. *Mol Ther* 14, 463-70 (2006).
40. Robbins, M. A. et al. Stable expression of shRNAs in human CD34+ progenitor cells can avoid induction of interferon responses to siRNAs in vitro. *Nat Biotechnol* 24, 566-71 (2006).
41. Ellington, A. D. & Szostak, J. W. In vitro selection of RNA molecules that bind specific ligands. *Nature* 346, 818-22 (1990).
42. Tuerk, C. & Gold, L. Systematic evolution of ligands by exponential enrichment: RNA ligands to bacteriophage T4 DNA polymerase. *Science* 249, 505-10 (1990).
43. Fitzwater, T. & Polisky, B. A SELEX primer. *Methods Enzymol* 267, 275-301 (1996).
44. Tuerk, C., MacDougal, S. & Gold, L. RNA pseudoknots that inhibit human immunodeficiency virus type 1 reverse transcriptase. *Proc Natl Acad Sci USA* 89, 6988-92 (1992).
45. Hicke, B. J. & Stephens, A. W. Escort aptamers: a delivery service for diagnosis and therapy. *J Clin Invest* 106, 923-8 (2000).
46. Pestourie, C., Tavitian, B. & Duconge, F. Aptamers against extracellular targets for in vivo applications. *Biochimie* 87, 921-30 (2005).
47. Nimjee, S. M., Rusconi, C. P. & Sullenger, B. A. Aptamers: an emerging class of therapeutics. *Annu Rev Med* 56, 555-83 (2005).
48. Proske, D., Blank, M., Buhmann, R. & Resch, A. Aptamers—basic research, drug development, and clinical applications. *Appl Microbiol Biotechnol* 69, 367-74 (2005).
49. Weiss, C. D. & White, J. M. Characterization of stable Chinese hamster ovary cells expressing wild-type, secreted, and glycosylphosphatidylinositol-anchored human immunodeficiency virus type 1 envelope glycoprotein. *J Virol* 67, 7060-6 (1993).
50. Vodicka, M. A. et al. Indicator cell lines for detection of primary strains of human and simian immunodeficiency viruses. *Virology* 233, 193-8 (1997).
Amarzguioui, M. et al. (2003). Tolerance for Mutation and Chemical Modifications in a siRNA. *Nucleic Acids Research* 31:589-595.
Eckstein, F. (2000). Phosphorothioate oligodeoxynucleotides: what is their origin and what is unique about them? *Antisense Nucleic Acid Drug Dev* 10:117-21
Herdewijn, P. (2000). Heterocyclic modifications of oligonucleotides and antisense technology. *Antisense Nucleic Acid Drug Dev* 10:297-310.
Kreuter, J. (1991) Nanoparticles-preparation and applications. *In: Microcapsules and nanoparticles in medicine and pharmacy*, Donbrow M., ed, CRC Press, Boca Raton, Fla., pp. 125-14.
Rusckowski, M. et al. (2000). Biodistribution and metabolism of a mixed backbone oligonucleotide (GEM 231) following single and multiple dose administration in mice. *Antisense Nucleic Acid Drug Dev* 10:333-345.
Stein, D. A. et al. (2001). Inhibition of Vesivirus infections in mammalian tissue culture with antisense morpholino oligomers. *Antisense Nucleic Acid Drug Dev* 11:317-25.
Vorobjev, P. E. et al. (2001). Nuclease resistance and RNase H sensitivity of oligonucleotides bridged by oligomethylenediol and oligoethylene glycol linkers. *Antisense Nucleic Acid Drug Dev* 11:77-85.

What is claimed is:

1. A molecule comprising an aptamer linked to a Dicer substrate siRNA, wherein the aptamer is an anti-HIV gp120 aptamer and wherein the Dicer substrate siRNA is a double stranded nucleic acid that targets an HIV-1 target sequence, wherein the HIV-1 target sequence is tat/rev, and wherein the Dicer substrate siRNA comprises the sequence:

(nucleotides 82-108 of SEQ ID NO: 1)
5' GCGGAGACAGCGACGAAGAGCUCAUCA 3'

(SEQ ID NO: 2)
3' CGCCUCUGUCGCUGCUUCUCGAGUAGUTT 5'.

2. A molecule comprising an aptamer linked to a Dicer substrate siRNA, wherein the aptamer is an anti-HIV gp120 aptamer and wherein the Dicer substrate siRNA is a double stranded nucleic acid that targets an HIV-1 target sequence, wherein the aptamer directs cell-specific delivery of the molecule when administered to a mammalian cell infected by HIV-1, wherein the HIV-1 target sequence is tat/rev, and wherein the Dicer substrate siRNA comprises the sequence:

(nucleotides 82-108 of SEQ ID NO: 1)
5' GCGGAGACAGCGACGAAGAGCUCAUCA 3'

(SEQ ID NO: 2)
3' CGCCUCUGUCGCUGCUUCUCGAGUAGUTT 5'.

3. A molecule comprising an aptamer linked to a Dicer substrate siRNA, wherein the aptamer is an anti-HIV gp120 aptamer and wherein the Dicer substrate siRNA is a double stranded nucleic acid that targets an HIV-1 target sequence, wherein each strand of the Dicer substrate siRNA comprises a 5' end and a 3' end and wherein the 5' end of one strand is linked to the aptamer, wherein the HIV-1 target sequence is tat/rev, and wherein the Dicer substrate siRNA comprises the sequence:

(nucleotides 82-108 of SEQ ID NO: 1)
5' GCGGAGACAGCGACGAAGAGCUCAUCA 3'

(SEQ ID NO: 2)
3' CGCCUCUGUCGCUGCUUCUCGAGUAGUTT 5'.

4. A method of cell-specific delivery of siRNA comprising administering a molecule to a mammalian cell infected by HIV-1, wherein the molecule comprises an aptamer linked to a Dicer substrate siRNA, wherein the aptamer is an anti-HIV gp120 aptamer and wherein the Dicer substrate siRNA is a double stranded nucleic acid that targets an HIV-1 target sequence, wherein the HIV-1 target sequence is tat/rev, and wherein the Dicer substrate siRNA comprises the sequence:

```
                    (nucleotides 82-108 of SEQ ID NO: 1)
5' GCGGAGACAGCGACGAAGAGCUCAUCA 3'

(SEQ ID NO: 2)
3' CGCCUCUGUCGCUGCUUCUCGAGUAGUTT 5'.
```

5. A method of cell-specific delivery of siRNA comprising administering a molecule to a mammalian cell infected by HIV-1, wherein the molecule comprises an aptamer linked to a Dicer substrate siRNA, wherein the aptamer is an anti-HIV gp120 aptamer and wherein the Dicer substrate siRNA is a double stranded nucleic acid that targets an HIV-1 target sequence, wherein the aptamer directs cell-specific delivery of the molecule to the mammalian cell, wherein the HIV-1 target sequence is tat/rev, and wherein the Dicer substrate siRNA comprises the sequence:

```
                    (nucleotides 82-108 of SEQ ID NO: 1)
5' GCGGAGACAGCGACGAAGAGCUCAUCA 3'

(SEQ ID NO: 2)
3' CGCCUCUGUCGCUGCUUCUCGAGUAGUTT 5'.
```

* * * * *

UNITED STATES PATENT AND TRADEMARK OFFICE
CERTIFICATE OF CORRECTION

PATENT NO. : 8,030,290 B2
APPLICATION NO. : 12/328994
DATED : October 4, 2011
INVENTOR(S) : John J. Rossi et al.

It is certified that error appears in the above-identified patent and that said Letters Patent is hereby corrected as shown below:

In the Specification

Column 1, Lines 15-18:
"The present invention was made in part with Government support under Grant Numbers AI29329 awarded by the National Institutes of Health, Bethesda, Md. The Government has certain rights in this invention."

Should be:
-- This invention was made with government support under AI029329 awarded by the National Institutes of Health. The government has certain rights in the invention. --

Signed and Sealed this
Third Day of October, 2023

Katherine Kelly Vidal
Director of the United States Patent and Trademark Office